United States Patent
Zhan et al.

(10) Patent No.: US 9,081,736 B2
(45) Date of Patent: Jul. 14, 2015

(54) MODELING OF MPGES-1 THREE-DIMENSIONAL STRUCTURES: APPLICATIONS IN DRUG DESIGN AND DISCOVERY

(75) Inventors: Chang-Guo Zhan, Lexington, KY (US); Xiaoqin Huang, Lexington, KY (US); Adel Hamza, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 13/064,594

(22) Filed: Apr. 1, 2011

(65) Prior Publication Data

US 2011/0288844 A1     Nov. 24, 2011

Related U.S. Application Data

(62) Division of application No. 11/698,230, filed on Jan. 24, 2007, now abandoned.

(51) Int. Cl.
| | |
|---|---|
| *G06G 7/48* | (2006.01) |
| *G06F 19/16* | (2011.01) |
| *C07K 1/00* | (2006.01) |
| *C12N 9/90* | (2006.01) |
| *G06F 19/22* | (2011.01) |

(52) U.S. Cl.
CPC . *G06F 19/16* (2013.01); *C07K 1/00* (2013.01); *C12N 9/90* (2013.01); *C12Y 503/99003* (2013.01); *G06F 19/22* (2013.01)

(58) Field of Classification Search
CPC ................................ G06F 19/10; G06F 19/16
See application file for complete search history.

(56) References Cited

U.S. PATENT DOCUMENTS 7,045,537 B1    5/2006   Woolfson et al.

OTHER PUBLICATIONS

Arnold et al. The Swiss-Model workspace: a web-based environment for protein structure homology modelling. Bioinformatics (2006) 22 (2): 195-201.*
Holm et al. Biochimica Biophysica Acta, vol. 1594, Issue 2, 2002, pp. 276-285.*
Thoren et al. J. Biol. Chemistry, vol. 278, No. 25, pp. 22199-22209, 2003.*
Huang et al. Bioorganic & Medicinal Chemistry, 2006, 14(10), 3553-3562.*

* cited by examiner

*Primary Examiner* — Michael Borin
(74) *Attorney, Agent, or Firm* — Crowell & Moring LLP

(57) ABSTRACT

This invention relates to representations of prostaglandin synthase three-dimensional structures. Such representations are suitable for designing agents that modulate the activity of the enzyme by binding to the substrate binding domain.

26 Claims, 13 Drawing Sheets

```
                         ┌──────── Helix A ────────┐
   MGST1    MVDLTQVMDDEVFMAFASYATIILSKMMILMSTATAFYRLT  40
   mPGES-1  MPAHSLVMSSPALPAFLLCSTLLVIKMYVVAIITGQVRLR   40
             *   : **.. .: **:   :*:::  **  ::: .*.   **
                                                        36

MGST1    RKVFANPEDCVAFGKGENAKKYLRTDDRVERVRRAHLNDL  80
   mPGES-1  KKAFANPEDALRHG----GPQYCRSDPDVERCLRAHRNDM  76
            :*.******.:  .*     . :* *:* .***   *** **:

┌──── Helix B ────┐  ┌──── Helix C ────┐
   MGST1    ENIIPFLGIGLLYSLSGPDPSTAILHFRLFVGARIYHTIA 120
   mPGES-1  ETIYPFLFLGFVYSFLGPNPFVAWMHFLVFLVGRVAHTVA 116
            *.* *** :*::**: **:* .*.:** :*: .*; **:*
                                                110   114

┌──────── Helix D ────────┐
   MGST1    YLTPLPQPNRALSFFVGYGVILSMAYRLL-KSKLYL 155
   mPGES-1  YLGKLRAPIRSVTYTLAQLPCASMALQILWEAARHL 152
            **  *  * *:::; :. .  :*** ::* ::  :*
                          130   134

Fig. 1
```

```
                    10        20        30        40        50        60        70
              ....|....|....|....|....|....|....|....|....|....|....|....|....|....|
1OCC.pdb      MFINRN---LFSTNKDIGTLYLLFGAMAGMVGTALGLLIRAELGQPGTL------------LGDDQI
hMPGES1       ------MPAHSLVMSSPALPAFLLCSTLLVIKMYVVAIITGQVRLRKKAFANPEDALRHGGPQYCRSDPD 80        90       100       110       120       130       140
              ....|....|....|....|....|....|....|....|....|....|....|....|....|....|
1OCC.pdb      YNVVVTAHAFVMIFFMVMPIMIGGFGNWLVPLMI-GAPDMAFPRMNNMSFWLLPPSFLLLLASSMVEAGA
hMPGES1       VERCLRAHRNDMETIYPFLFLGFVYSF-------LGPRFVAHMRLVFLVGRVAMTVATL----------

150       160       170       180       190       200       210
              ....|....|....|....|....|....|....|....|....|....|....|....|....|....|
1OCC.pdb      GTGWTVYPPLAGNLAHAGASVDLTIFSLHLAGVSSILGAINFITTIINMKPP----------------
hMPGES1       -----------GKLRAPI---RSVTYTLAQLFCASMALQIL--------NESARHL-----------
```

Fig. 12

MODELING OF MPGES-1 THREE-DIMENSIONAL STRUCTURES: APPLICATIONS IN DRUG DESIGN AND DISCOVERY

CROSS REFERENCE TO RELATED APPLICATIONS

This application is a divisional of U.S. application Ser. No. 11/698,230, filed Jan. 24, 2007, the entire disclosure of which is incorporated herein by reference.

TECHNICAL FIELD

Computational methods for determining the three-dimensional structure of one or more polypeptides are provided. Also provided are three-dimensional models of a microsomal prostaglandin synthase molecule and computer-implemented methods for identifying compounds that interact with the molecule.

BACKGROUND

Prostaglandin (PG) E2 is produced by a variety of cells and tissues and exhibits potent diverse bioactivities. Its production is mediated by three enzymatic reactions involving phospholipase A2 (PLA2), cyclooxygenase (COX), and PGE2 synthase (PGES). In this biosynthetic pathway, arachidonic acid (AA) releases from membrane phospholipids by cytosolic or secretory PLA2 and is converted to prostaglandin H2 (PGH2) by COXs. PGH2 is then isomerized to prostaglandin E2 (PGE2) by terminal PGES enzymes. PGES enzymes, that lie downstream of COXs, occur in three forms in mammalian cells. Among them, the microsomal and membrane-bound synthase (namely mPGES-1) has received much more attention and established as a novel drug target in the areas of inflammation, tumorigenesis, and bone disorders. Hence, mPGES-1 is involved in a number of diseases including arthritis, burn injury and pain diseases, atherosis, cancer, and even the exacerbation of Alzheimer's disease. Recently reported studies have led to the characterization of its inducible distribution, expression, enzymatic kinetics, and biological and pathological functions. The expression of mPGES-1 is up-regulated by pro-inflammatory stimuli and down-regulated by anti-inflammatory glucocorticoids, often in accordance with that of COX-2. The protein mPGES-1 has been identified as the central switch during immune-induced pyresis, and deletion of mPGES-1 would reduce inducible and basal PGE2 production and alter the gastric prostanoid profile. Compared to its up-stream enzymes, inhibition of mPGES-1 does not block normal functions of other PGs and, therefore, lacks the unexpected side effects produced by the inhibition of COXs, making it more attractive for the development of potential therapeutics, especially for the treatment of inflammation-related diseases. However, no clinically useful inhibitor of mPGES-1 has been identified. To date, only two types of compounds, i.e. the COX-2 inhibitor NS-398 and 5-lipoxygenese-activating protein (FLAP) inhibitor MK-886 (see FIG. 9) and similar compounds (see e.g., Riendeau et al., Bioorg. Med. Chem. Lett., 15:3352-3355), have been found to be able to inhibit mPGES-1. None of these compounds is selective for mPGES-1. It is highly desirable to develop more potent and selective inhibitors of mPGES-1 based on the structure and function of the enzyme for development of the next-generation therapeutics.

Initially, mPGES-1 was discovered as recombinant human microsomal glutathione-S-transferase (GST)-1-like 1 (MGST1-L1) and recognized as a member of membrane-associated proteins involved in eicosanoid and glutathione (GSH) metabolism (MAPEG) superfamily. It shows significant homology with other MAPEG proteins, especially with the nearest subfamily member MGST1. Hydropathy analysis suggests that all the MAPEG proteins have similar three-dimensional and membrane-spanning topological properties. Site-directed mutagenesis revealed that R110 has an essential role in the catalytic function of mPGES-1, whereas the mutation on either R51 or R70 did not affect the activity. Unfortunately, further structure-function investigation is restrained by the lack of the detailed three-dimensional structure of this membrane-bound protein, making the structure-based design of drugs targeting mPGES-1 difficult. A two-dimensional (2D) electron projection map (with a resolution of 10 Å) of mPGES-1 revealed a trimer structure (Thoren, et al., J. Biol. Chem. 2003, 278, 22199-22209) which is very similar to that of MGST1, but the resolution of 10 Å is insufficient for the purpose of building a three-dimensional model of mPGES-1.

Accordingly, more precise models of the three-dimensional structure of mPGES-1 are needed so that potent and selective modulators of mPGES-1 activity can be identified.

SUMMARY

Provided herein are three-dimensional structures of the substrate binding domain (SBD) of the microsomal prostaglandin E2 synthase-1 (mPGES-1), and three-dimensional structures of mPGES-1 trimers, useful for designing and identifying compounds that modulate the activity of the synthase. Also provided are novel methods for generating a set of candidate structures of mPGES-1, the mPGES-1 substrate binding domain (SBD) and mPGES-1 trimers. Also provided are methods of identifying compounds that bind to an mPGES-1 structure provided herein, including those that bind to the SBD of mPGES-1.

Accordingly, in one embodiment a method for identifying a set of candidate structures includes a) obtaining a first amino acid sequence derived from a query polypeptide; b) obtaining a second amino acid sequence derived from a template polypeptide, wherein the second sequence comprises: i) a predetermined three-dimensional structure; and ii) at least 50% sequence homology with the first sequence; c) performing a sequence alignment between the first sequence and the second sequence, and identifying common secondary structures; d) generating a plurality of candidate topological structures by applying predetermined geometric parameters to the secondary structures and transforming each topological structure into the amino acid residues associated with the secondary structures; e) generating a first conformation set by screening the plurality of candidate topological structures with the predetermined geometric parameters and identifying the structures that correspond to the parameters; f) generating a second conformation set by applying energy minimization functions to the first conformation set and identifying energetically-favored conformations; and g) generating a final conformation set by selecting those structures that exhibit an energy gradient having a root mean square deviation (RMSD) of less than 0.001 kcal mol$^{-1}$ Å$^{-1}$, wherein the final conformation set represents the set of candidate structures of the query polypeptide.

In some embodiments, methods of identifying a set of candidate structures of a polypeptide further include generating the sequence alignment by generating the reciprocal position of the conserved residues. In other embodiments, such methods further include modeling the interaction of each member of the final conformation set with at least one substrate, wherein the modeling comprises molecular docking using binding site searching and/or interaction energy scoring; and identifying amino acid residues associated with the SBD that interact with the substrate.

In other embodiments, the methods further include identifying at least one amino acid residue that interacts with the substrate and determining the effect of the modification on substrate binding to the modified polypeptide. In general the modification is a substitution, such as a conservative or non-conservative amino acid substitution. In yet another embodiment, the methods further include producing the modified polypeptide in vivo or in vitro and assaying the activity of the modified polypeptide in vivo or in vitro.

In one aspect, a query polypeptide includes membrane-spanning regions of amino acids. Such polypeptides include the membrane-associated proteins involved in eicosanoid and glutathione metabolism (MAPEG). In other aspects, the query polypeptide is microsomal prostaglandin E synthase-1 (mPGES-1).

In another aspect, the template polypeptide is a member of the membrane-associated proteins involved in eicosanoid and glutathione metabolism (MAPEG), such as microsomal glutathione-S-transferase-1 (MGST-1). Structural parameters can include coordinates derived from 3D electron projection maps of a template polypeptide, such as MGST1. In some aspects, the structural parameters further include coordinates derived from 2D electron projection maps of the query polypeptide, such as mPGES-1. Structural parameters can correspond to the coordinates set forth in Table 1.

In another embodiment, a representation of a three-dimensional structure of the mPGES-1 substrate binding domain (SBD) is provided. The representation is characterized in that: a) amino acid residues Q36, R110, T114, Y130, and Q134 of mPGES-1 are associated with the PGH2-binding site of the SBD; b) amino acid residue Y130 of mPGES-1 are associated with the peroxy head of prostaglandin H2 (PGH2) when PGH2 occupies at least a portion of the binding site; c) amino acid residue Y130 of mPGES-1 is associated with the —SH group of glutathione (GSH) when GSH occupies at least a portion of the binding site; d) amino acid residues R110, T114, and Q36 of mPGES-1 are associated with the carboxyl tail of PGH2; e) the calculated binding free energy ($\Box$G) for an SBD-PGH2 complex is between −5.0 kcal/mol and −9.0 kcal/mol; and f) the calculated binding free energy ($\Box$G) for an SBD-GSH complex is between −4.0 kcal/mol and −8.0 kcal/mol.

In another embodiment, a representation of a three-dimensional structure of an mPGES-1 trimer is provided. The representation is characterized in that: a) each monomer of the trimer comprises a representation of a three-dimensional structure of the mPGES-1 substrate binding domain (SBD); b) the trimer comprises $C_3$-fold symmetry; and c) the representation of the trimer comprises a homology model based on the crystallographic structure of subunit 1 of cytochrome c oxidase.

In yet another embodiment, a method of structure-based identification of candidate compounds for regulation of interactions of mPGES-1 with its cognate ligands, is provided. The method includes a) providing a three dimensional structure of mPGES-1, the three dimensional structure being selected from the group consisting of: i) the mPGES-1 substrate binding domain as set forth in claim 23; and ii) the mPGES-1 trimer as set forth in claim 25; b) identifying at least one candidate compound for interacting with the three dimensional structure of a) and performing structure based drug design.

In another embodiment, a machine-readable medium embedded with information that corresponds to the three-dimensional structural representation of the mPGES-1 substrate binding domain (SBD), is provided. Also provided is a machine-readable medium embedded with information that corresponds to the three-dimensional structural representation of the mPGES-1 trimer.

In one embodiment, a computer system including a representation of the three-dimensional structure of the mPGES-1 substrate binding domain (SBD) and a user interface to view the representation, is provided. Also provided is a computer system that includes a representation of the three-dimensional structure of the mPGES-1 trimer and a user interface to view the representation.

The various methods and computer-generated structures provided herein are suitable for use in conducting a biotechnology business. Such a business can include identifying one or more candidate compounds for regulation of interactions of mPGES-1 with its cognate ligands, generating a machine-readable medium, or data signal embodied in a carrier wave, embedded with information that corresponds to the three-dimensional structural representation of the candidate compound and providing the medium or data signal to an end user.

In general, structures derived from the computer-generated models provided herein encompass structures having coordinates that differ by a root mean square deviation (RMSD) of less than about 1.5 Å, 0.75 Å, or 0.35 Å, or any deviation in this range. In some aspects, the query polypeptide includes an amino acid sequence having at least 75%, at least 85%, or at least 95%, or any percent in this range, amino acid sequence identity to the template polypeptide.

In other embodiments, a structure of a synthase molecule provided herein also includes a ligand complexed with the synthase molecule. In some aspects, the ligand is a small molecule.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 depicts a sequence alignment of the mPGES-1 with MGST1. Stars refer to identical residues, whereas filled period or double filled period refer to conservative substitutions. All these positions (with stars and filled periods) give the total homology of mPGES-1 SEQ. I.D. No.: 12 with MGST1 SEQ. I.D. No.: 13 as 73%. Helices of mPGES-1 are labeled. Mutated residues are numbered below the sequence.

Figure 4A:
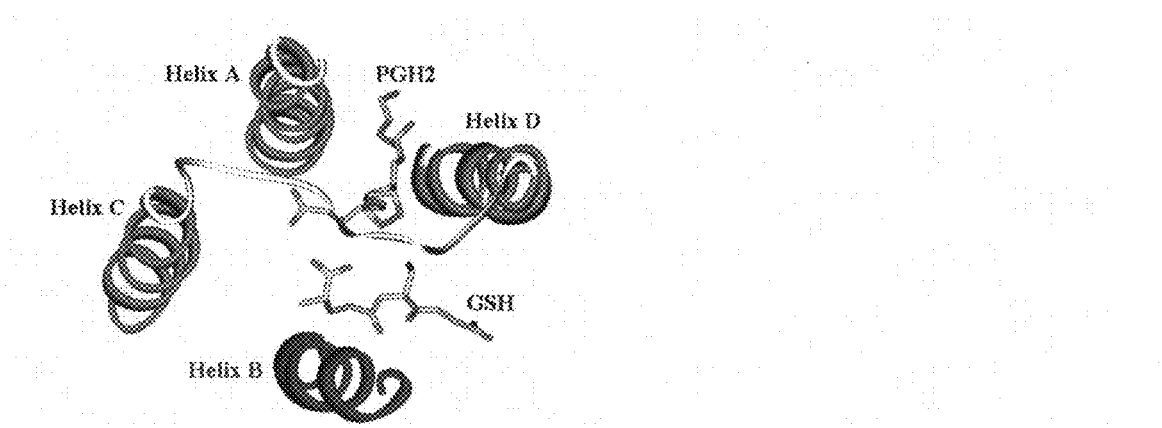
FIG. 4A depicts a top view from outside of the membrane of an optimized complex model of the SBD of mPGES-1 binding with substrates PGH2 and GSH. The SBD of mPGES-1 is represented as ribbon, and the two substrates are shown in stick.
Figure 4B:
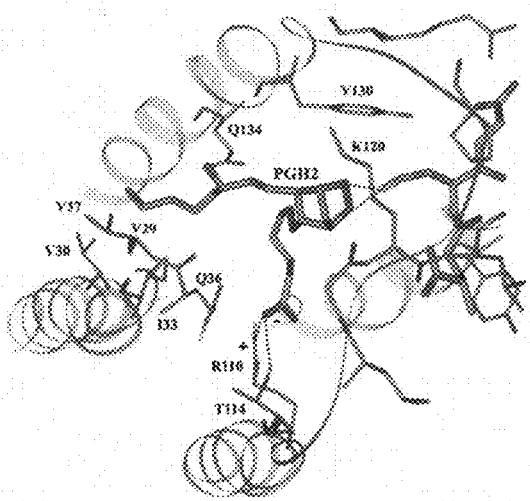

FIG. 4B depicts PGH2 binding with the enzyme. Residues in the SBD of mPGES-1 within 5 Å around PGH2 are shown and labeled in stick, the electrostatic interaction is represented as the plus (+) and minus (−) signs, and the hydrogen bonding is indicated with dashed line.

Figure 4C:
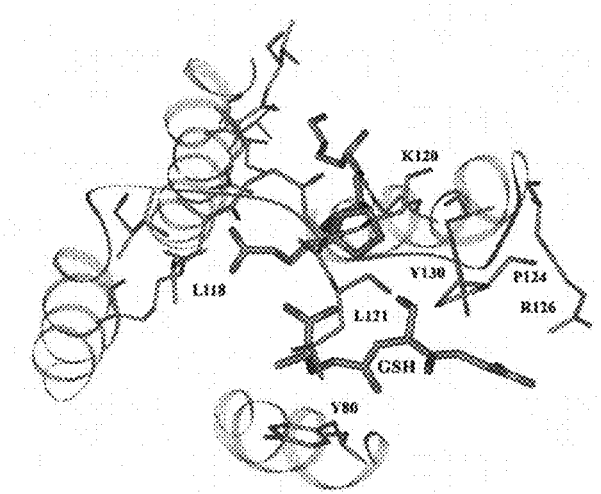

FIG. 4C depicts GSH binding with the SBD of mPGES-1. Residues in the SBD of mPGES-1 within 5 Å around GSH are shown and labeled.

Figure 5:
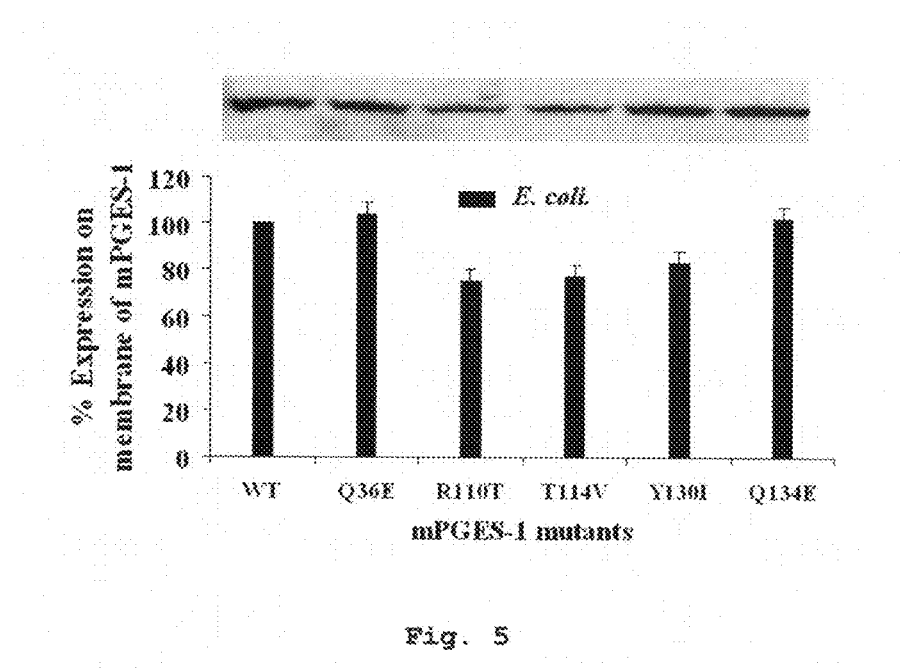

FIG. 5 depicts the cell membrane portion of mPGES-1 expression in *E. coli*. Bars represent the percentage of expression for the five mutants (Q36E, R110T, T114V, Y130I, and Q134E) relative to the wild-type (WT) of mPGES-1.

Figure 6:
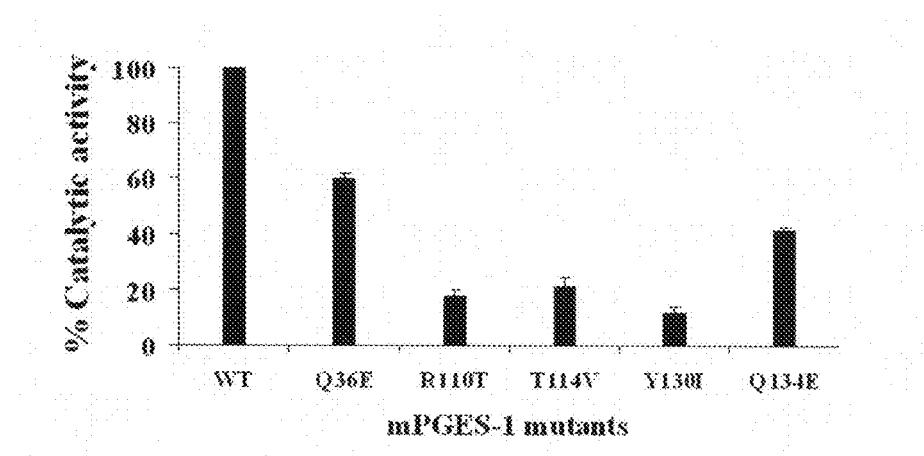

FIG. 6 depicts the relative enzymatic activity of mPGES-1 and its mutants. The relative activity is obtained by normalization from its expression level in FIG. 5 and the wild-type served as a standard of 100 units.

Figure 7:
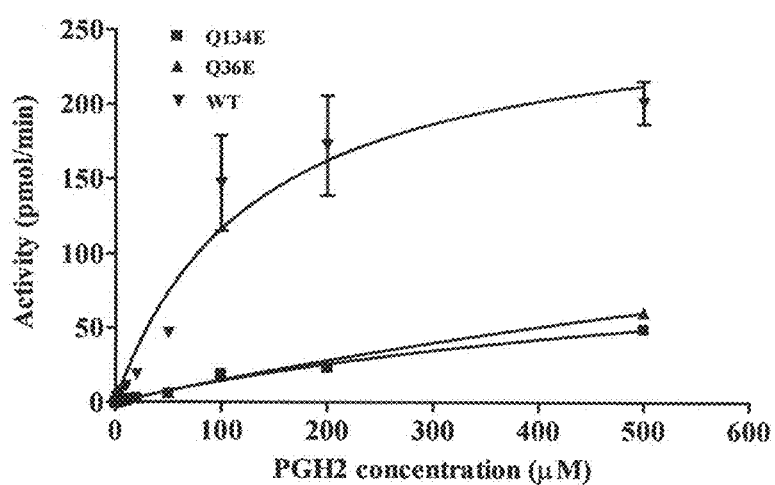

FIG. 7 depicts experimentally measured $K_M$ of mPGES-1 and its mutants.

Figure 8:
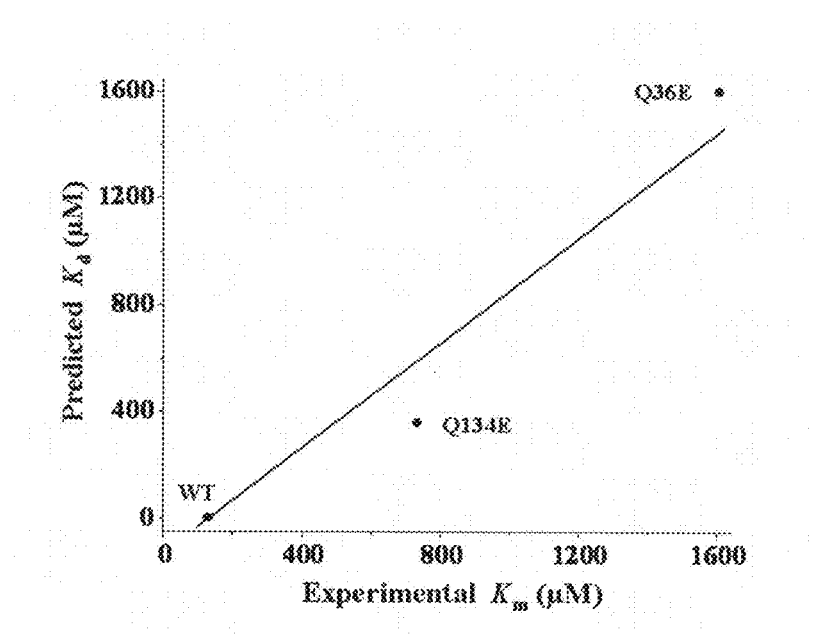

FIG. 8 depicts the calculated $K_d$ values of PGH2 binding with wild-type mPGES-1 and its mutants in comparison with the experimentally derived $K_M$.

Figure 9:
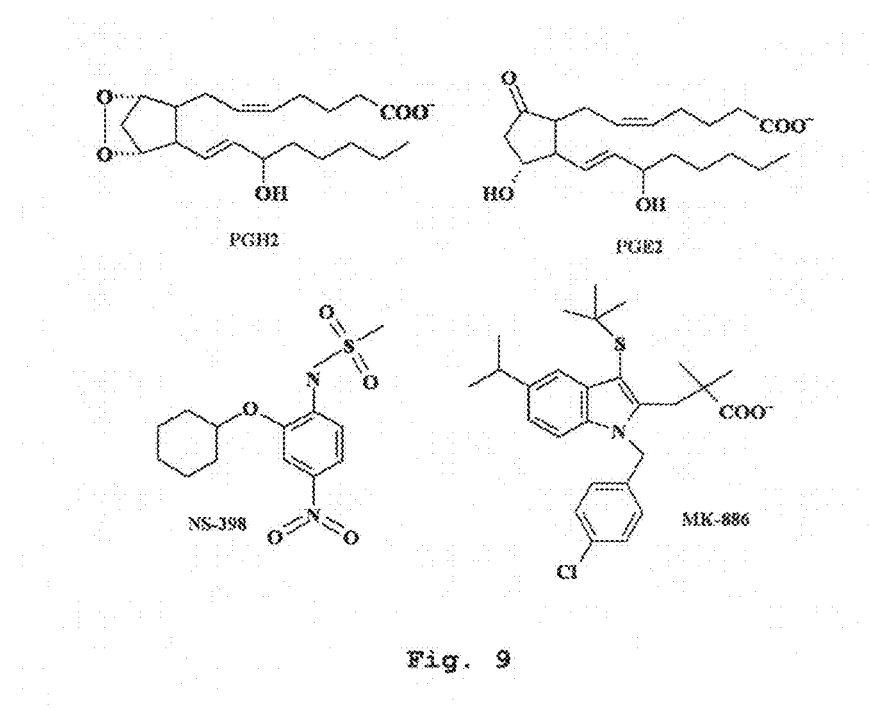

FIG. 9 depicts the chemical structures of PGH2, PGE2, and COX-2 inhibitors NS-398 and 5-lipoxygenese-activating protein (FLAP) inhibitor MK-886.

Figure 10:
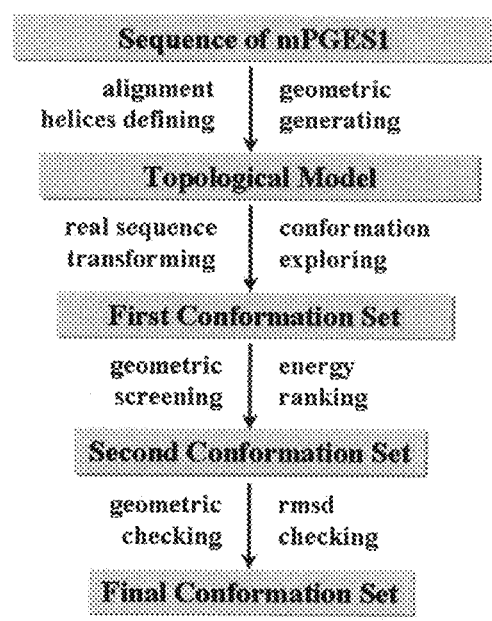

FIG. 10 depicts a flow diagram of an exemplary "ab initio" rationale for generating three-dimensional models of polypeptides.

Figure 11A:
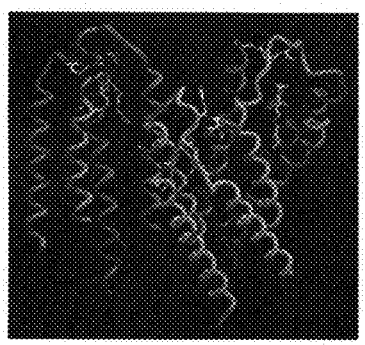

FIG. 11A depicts an exemplary view of three-dimensional model #1 obtained for the mPGES-1 trimer.

Figure 11B:
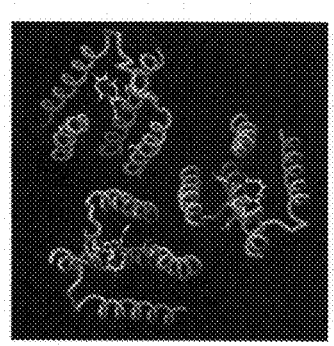

FIG. 11B depicts another an exemplary view of three-dimensional model #1 obtained for the mPGES-1 trimer.

Figure 11C:
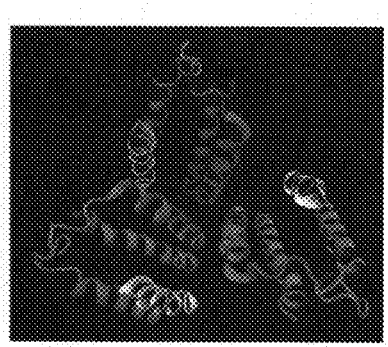

FIG. 11C depicts yet another exemplary view of three-dimensional model #1 obtained for the mPGES-1 trimer.

FIG. 12 depicts a sequence alignment of human mPGES-1 (SEQ ID NO:12) with the cytochrome c template (SEQ ID NO:11). The alpha-helices are underlined.

Figure 13A:
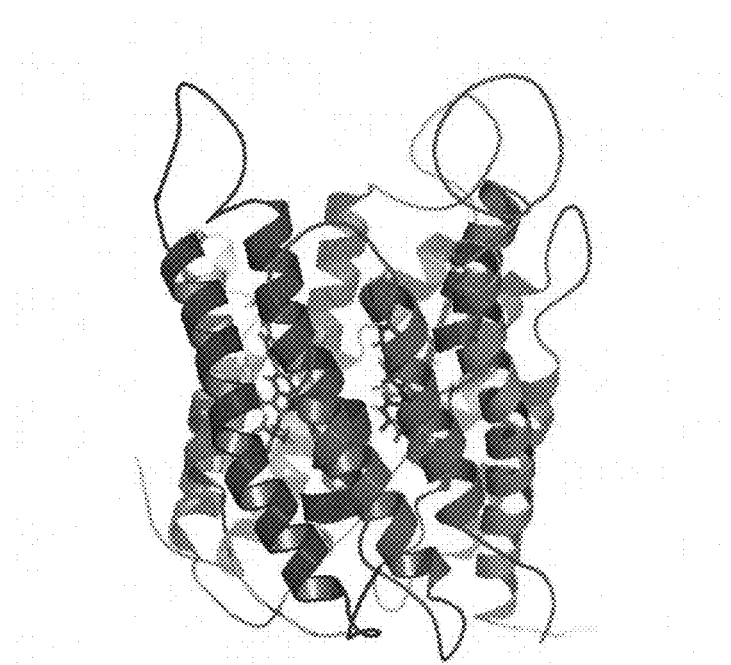
Figure 13B:
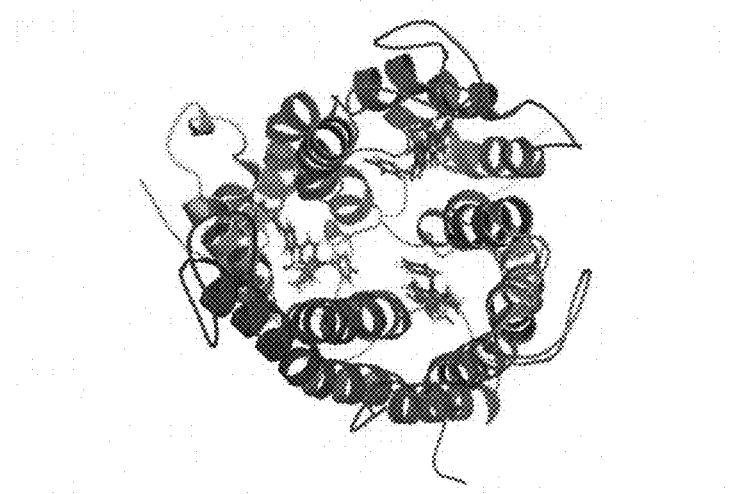

FIG. 13A and FIG. 13B depict three-dimensional model #2 of the mPGES-1 trimer complexed with an inhibitor (i.e. MK-886) in each substrate binding domain (SBD).

Like reference symbols in the various drawings indicate like elements.

DETAILED DESCRIPTION

Three-dimensional (3D) representations, methods, and computer programs for the ab initio prediction of three-dimensional structures of proteins are provided. Specifically, provided herein are representations of novel three-dimensional structures of a microsomal prostaglandin E synthase-1 (mPGES-1) molecule, and the structure of the mPGES-1 trimer. Also provided are methods of generating such representations and methods of using such information to identify, design and/or modify compounds that modulate the activity of an mPGES-1 molecule. In addition, computer systems that include such information are provided.

Throughout the present disclosure the term "microsomal prostaglandin E synthase-1 (mPGES-1) molecule" or "synthase molecule" are used describe various embodiments of the inventions. It is understood that these terms encompass a single molecule of mPGES-1 (e.g., a monomer), fragments of mPGES-1 (e.g., the substrate binding domain (SBD)), and/or multimers of mPGES-1 (e.g., an mPGES-1 trimer).

Methods of Identifying Sets of Conformations

Provided herein are computer-implemented methods for homology modeling by comparing the amino acid sequence of a query polypeptide (e.g., mPGES-1) with the amino acid sequence of a template polypeptide (e.g., a membrane-associated protein involved in eicosanoid and glutathione metabolism (MAPEG)). The query polypeptide shares sequence homology with the template polypeptide. Structural information associated with the template polypeptide (e.g., atomic coordinates based on NMR or x-ray crystallographic data) can be used to generate a model of the query polypeptide. The model can be further refined by subjecting the preliminary model to energy minimization to yield an energy minimized model and remodeling regions of the energy minimized model where stereochemistry restraints are violated. These refinements yield sets of conformations that can be further subjected to, for example, in silico interactions with a suitable substrate.

The term "protein" is understood to include the terms "polypeptide" and "peptide" (which, at times, may be used interchangeably herein) within its meaning. In addition, proteins comprising multiple polypeptide subunits (e.g., dimers, trimers or tetramers), as well as other non-proteinaceuos catalytic molecules will also be understood to be included within the meaning of "protein" as used herein. Similarly, "protein fragments," i.e., stretches of amino acid residues that comprise fewer than all of the amino acid residues of a protein, are also within the scope of the invention and may be referred to herein as "proteins." Additionally, "protein domains" are also included within the term "protein." A "protein domain" represents a portion of a protein comprised of its own semi-independent folded region having its own characteristic spherical geometry with hydrophobic core and polar exterior.

The methods provided herein can be employed in those cases where a sequence comparison indicates possible local structural similarity of the query protein to protein(s) of known structure. For example, a small structural motif (a long helix, helical hairpin, fragment of a beta-sheet) can be used as a modeling "template". Such a template can provide a folding scaffold, thereby reducing the conformational space to be searched in order to assemble the remaining portions of the structure of the query protein.

The structural motif can be associated with, for example, a "functional site." The term "functional site" or "functional domain" generally refer to any site in a protein that confers a function on the protein. Representative examples include active sites (i.e., those sites in catalytic proteins where catalysis occurs), protein-protein interaction sites, sites for chemical modification (e.g., glycosylation and phosphorylation sites), and ligand binding sites. Ligand binding sites include, but are not limited to, metal binding sites, co-factor binding sites, antigen binding sites, substrate channels and tunnels, and substrate binding domains (SBD). In an enzyme, a ligand binding site that is a substrate binding domain may also be an active site. Functional sites may also be composites of multiple functional sites, wherein the absence of one or more sites comprising the composite results in a loss of function. Identifying compounds that bind to a functional site, such as a substrate binding domain, are discussed below.

Accordingly, in one embodiment a method for identifying a set of candidate structures includes a) obtaining a first amino acid sequence derived from a query polypeptide; b) obtaining a second amino acid sequence derived from a template polypeptide, wherein the second sequence comprises: i) a predetermined three-dimensional structure; and ii) at least 50% sequence homology with the first sequence; c) performing a sequence alignment between the first sequence and the second sequence, and identifying common secondary structures; d) generating a plurality of candidate topological structures by applying predetermined geometric parameters to the secondary structures and transforming each topological structure in to the amino acid residues associated with the secondary structures; e) generating a first conformation set by screening the plurality of candidate topological structures with the predetermined geometric parameters and identifying the structures that correspond to the parameters; f) generating a second conformation set by applying energy minimization functions to the first conformation set and identifying energetically-favored conformations; and g) generating a final conformation set by selecting those structures that exhibit an energy gradient having a root mean square deviation (RMSD) of less than 0.001 kcal mol-1 Å-1, wherein the final conformation set represents the set of candidate structures of the query polypeptide.

Identifying a set of candidate structures is based, in part, on computer generated structures derived, in part, from crystal structures of homologous proteins (i.e., "homologs"). As used herein, the term "homolog" refers to the polypeptide molecule, or a functional domain from said polypeptide from a first source having at least about 30%, 40% or 50% sequence identity, or at least about 60%, 70% or 75% sequence identity, or at least about 80% sequence identity, or more preferably at least about 85% sequence identity, or even more preferably at least about 90% sequence identity, and most preferably at least about 95%, 97% or 99% amino acid sequence identity with the polypeptide, or any functional domain thereof, from a second source. The second source may be a version of the molecule from the first source that has been genetically altered by any available means to change the primary amino acid or may be from the same or a different species than that of the first source.

As previously mentioned, a template polypeptide includes a "predetermined three-dimensional structure." As used herein, a "predetermined three-dimensional structure" includes crystalline forms of a polypeptide provided as data in the form of structure coordinates. As used herein, the term "atomic coordinates" or "structure coordinates" refers to mathematical coordinates that describe the positions of atoms in a crystal in a Protein Data Bank (PDB) format, including X, Y, Z and B, for each atom. The diffraction data obtained from the crystals are used to calculate an electron density map of the repeating unit of the crystal. The electron density maps may be used to establish the positions (i.e., coordinates X, Y and Z) of the individual atoms within the crystal.

The computer-generated structure coordinates identified for a query polypeptide, or sets or polypeptides, based upon the coordinates available from a template polypeptide, or an active site thereof, define a unique configuration of points in space. Those of skill in the art understand that a set of structure coordinates for a polypeptide, or a polypeptide complexed with a chemical entity, or a portion thereof, define a relative set of points that, in turn, define a configuration in three dimensions. A similar or identical configuration can be defined by an entirely different set of coordinates, provided the distances and angles between coordinates remain essentially the same. Accordingly, the coordinates provide a "scalable" configuration of points that can be modified by increasing or decreasing the distances between coordinates by a scalar factor while keeping the angles essentially the same.

For example, in identifying sets of conformationally suitable structures, it may be desirable to identify "conformational" or "secondary" constraints. These terms refer to the presence of a particular protein conformation, for example, an alpha-helix, parallel and anti-parallel beta strands, leucine zipper, zinc finger, etc. in which an amino acid residue, or group of residues, is located. In addition, conformational or secondary constraints can include amino acid sequence information without additional structural information. As an example, "-C-X-X-C-" is a conformational constraint indicating that two cysteine residues must be separated by two other amino acid residues, the identities of each of which are irrelevant in the context of this particular constraint.

An "identity constraint" refers to a constraint that indicates the identity of a particular amino acid residue at a particular amino acid position in a protein. Typically, an amino acid position is determined by counting from the amino-terminal residue of the protein up to and including the residue in question. As those in the art will appreciate, comparison between related proteins may reveal that the identity of a particular amino acid residue at a given amino acid position in a protein is not entirely conserved, i.e., different amino acid residues may be present at a particular amino acid position in related proteins, or even in allelic or other variants of the same protein.

In another embodiment, methods of identifying a set of candidate structures of a polypeptide further include modeling the interaction of each member of a final conformation set with at least one "substrate" or "cognate ligand." Such modeling can be in the form of molecular docking using binding site searching and/or interaction energy scoring. The amino acid residues associated with the SBD, and that interacts with the substrate, can be identified.

A "functional site" refers to any site in a protein that has a function. Representative examples include active sites (i.e., those sites in catalytic proteins where catalysis occurs), protein-protein interaction sites, sites for chemical modification (e.g., glycosylation and phosphorylation sites), and substrate binding sites. Substrate binding sites include, but are not limited to, metal binding sites, co-factor binding sites, antigen binding sites, substrate channels and tunnels, and ligand binding sites. In an enzyme, a substrate binding site may also be an active site.

The methods provided herein include using a known ligand that binds to both the query polypeptide and template polypeptide in order to further refine the structure of the query polypeptide. Accordingly, the structure of the substrate binding domain (SBD) of an mPGES-1 molecule can be delineated using mPGES-1 cognate ligands (e.g., PGH2 and GSH).

Active sites, such as substrate binding domains, are of significant utility in the identification of compounds that specifically interact with, and modulate the activity of, a particular polypeptide. The association of natural ligands or substrates with the active sites of their corresponding receptors or enzymes is the basis of many biological mechanisms of action. Similarly, many compounds exert their biological effects through association with the active sites of receptors and enzymes. Such associations may occur with all or any parts of the active site. An understanding of such associations helps lead to the design of compounds that modulate the activity of their target. Therefore, this information is valuable in designing potential modifiers of mPGES-1 activity, as discussed in more detail below.

In other embodiments, the methods further include identifying at least one amino acid residue that interacts with the substrate, modifying the residue, and determining the effect of the modification on substrate binding to the modified polypeptide. In general the modification is a substitution, such as a conservative or non-conservative amino acid substitution. It may be desirable to make mutations in the active site of a polypeptide, e.g., to increase, reduce or completely eliminate synthase activity. Mutations that will reduce or completely eliminate the activity of mPGES-1 are provided in the examples below. Such mutations can be introduced into a computer generated structural representation of a molecule. Such "in silico" mutagenesis can be used to confirm or augment the computer generated structural representation of, for example, the mPGES-1 molecule. In vivo and in vitro mutagenesis can be used to further confirm or augment the information generated in silico. Such mutations are discussed further in the examples provided below.

In yet another embodiment, the methods further include producing the modified polypeptide in vivo or in vitro and assaying the activity of the modified polypeptide in vivo or in vitro. Methods of producing modified polypeptides in vivo or in vitro are well known to the skilled artisan. Examples of such methods are provided below.

In general amino acid modifications include substitutions of one amino acid for another. Such substitutions, whether manufactured in silico, in vitro, or in vivo, generally include conservative and non-conservative amino acid substitutions.

As used herein, an "amino acid" is a molecule having the structure wherein a central carbon atom (the alpha-carbon atom) is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino and carboxylic groups in the dehydration reaction that links one amino acid to another. As a result, when incorporated into a protein, an amino acid is referred to as an "amino acid residue." In the case of naturally occurring proteins, an amino acid residue's R group differentiates the 20 amino acids from which proteins are synthesized, although one or more amino acid residues in a protein may be derivatized or modified following incorporation into protein in biological systems (e.g., by glycosylation and/or by the formation of cysteine through the oxidation of the thiol side chains of two non-adjacent cysteine amino acid residues, resulting in a disulfide covalent bond that frequently plays an important role in stabilizing the folded conformation of a protein, etc.). As those in the art will appreciate, non-naturally occurring amino acids can also be incorporated into proteins, particularly those produced by synthetic methods, including solid state and other automated synthesis methods. Examples of such amino acids include, without limitation, alpha-amino isobutyric acid, 4-amino butyric acid, L-amino butyric acid, 6-amino hexanoic acid, 2-amino isobutyric acid, 3-amino propionic acid, ornithine, norlensine, norvaline, hydroxproline, sarcosine, citralline, cysteic acid, t-butylglyine, t-butylalanine, phenylylycine, cyclohexylalanine, beta-alanine, fluoro-amino acids, designer amino acids (e.g., beta-methyl amino acids, alpha-methyl amino acids, alpha-methyl amino acids) and amino acid analogs in general. In addition, when an alpha-carbon atom has four different groups (as is the case with the 20 amino acids used by biological systems to synthesize proteins, except for glycine, which has two hydrogen atoms bonded to the carbon atom), two different enantiomeric forms of each amino acid exist, designated D and L. In mammals, only L-amino acids are incorporated into naturally occurring polypeptides. Of course, the instant invention envisions proteins incorporating one or more D- and L-amino acids, as well as proteins comprised of just D- or L-amino acid residues.

Conventional amino acid residue abbreviations are used throughout this patent, and both the one and three letter codes are reproduced here for convenience: alanine="A" or "Ala"; arginine="R" or "Arg"; asparagine="N" or "Asn"; aspartic acid="D" or "Asp"; cysteine="C" or "Cys"; glutamic acid="E" or "Glu" glutamine="Q" or "Gln"; glycine="G" or "Gly"; histidine="H" or "His"; isoleucine="I" or "Ile"; leucine="L" or "Leu"; lysine "K" or "Lys"; methionine="M" or "Met"; phenylalanine="F" of "Phe"; proline "P" or "Pro"; serine="S" or "Ser"; threonine="T" or "Thr"; tryptophan="W" or "Trp"; tyrosine="Y" or "Tyr"; and valine="V" or "Val". Amino acid sequences are written from amino to carboxy-terminus, unless otherwise indicated. Conventional nucleic acid nomenclature is also used, wherein "A" means adenine, "C" means cytosine, "G" means guanine, "T" means thymine, and "U" means uracil. Nucleotide sequences are written from 5' to 3', unless otherwise indicated.

Conservative amino acid substitutions are well-known in the art, and include substitutions made on the basis of a similarity in polarity, charge, solubility, hydrophobicity and/or the hydrophilicity of the amino acid residues involved. Typical conservative substitutions are those in which the amino acid is substituted with a different amino acid that is a member of the same class or category, as those classes are defined herein. Thus, typical conservative substitutions include aromatic to aromatic, apolar to apolar, aliphatic to aliphatic, acidic to acidic, basic to basic, polar to polar, etc. Other conservative amino acid substitutions are well known in the art.

Structures

As those in the art are aware, protein structures can be of different quality. Presently, the highest quality determination methods are experimental structure prediction methods based on x-ray crystallography and/or NMR spectroscopy. In x-ray crystallography, "high resolution" structures are those wherein atomic positions are determined at a resolution of about 2 Å or less, and enable the determination of the three-dimensional positioning of each atom (or at least each non-hydrogen atom) of a protein. "Medium resolution" structures are those wherein atomic positioning is determined at about the 2-4 Å level, while "low resolution" structures are those wherein the atomic positioning is determined in about the 4-8 Å range. Herein, protein structures that have been determined by x-ray crystallography or NMR may be referred to as "template polypeptides" or "experimental structures," as compared to those determined by computational methods, i.e., derived from the application of one or more computer algorithms to a primary amino acid sequence to predict protein structure.

Accordingly, in another embodiment, a representation of a three-dimensional structure of the mPGES-1 substrate binding domain (SBD) is provided. The representation is characterized in that: a) amino acid residues Q36, R110, T114, Y130, and Q134 of mPGES-1 are associated with the PGH2-binding site of the SBD; b) amino acid residue Y130 of mPGES-1 are associated with the peroxy head of prostaglandin H2 (PGH2) when PGH2 occupies at least a portion of the binding site; c) amino acid residue Y130 of mPGES-1 is associated with the —SH group of glutathione (GSH) when GSH occupies at least a portion of the binding site; d) amino acid residues R110, T114, and Q36 of mPGES-1 are associated with the carboxyl tail of PGH2; e) the calculated binding free energy ($\Delta G$) for an SBD-PGH2 complex is between −5.0 kcal/mol and −9.0 kcal/mol; and f) the calculated binding free energy ($\Delta G$) for an SBD-GSH complex is between −4.0 kcal/mol and −8.0 kcal/mol.

In another embodiment, a representation of a three-dimensional structure of an mPGES-1 trimer is provided. The representation is characterized in that: a) each monomer of the trimer comprises a representation of a three-dimensional structure of the mPGES-1 substrate binding domain (SBD); b) the trimer comprises $C_3$-fold symmetry; and c) the representation of the trimer comprises a homology model based on the crystallographic structure of subunit 1 of cytochrome c oxidase.

As discussed throughout the specification, protein structures can be determined entirely by computational methods, including, but not limited to, homology modeling, threading, and ab initio methods. Often, models produced by such computational methods are "reduced" models. A "reduced model" refers to a three-dimensional structural model of a protein wherein fewer than all heavy atoms (e.g., carbon, oxygen, nitrogen, and sulfur atoms) of the protein are represented. For example, a reduced model might consist of just the alpha-carbon atoms of the protein, with each amino acid connected to the subsequent amino acid by a virtual bond. As will be appreciated by those in the art, more detailed model structures of a protein can be assembled from a reduced model. For example, a reduced model comprised only of amino acid residue side chain centers of mass implicitly specifies the location of the atoms comprising the side chain, as well the position of the peptide backbone. Accordingly, whatever greater level of atomic detail is required, if any, for the particular application can be added to a reduced model, and it is understood that once a protein structure based on a reduced model has been generated, all or a portion of it may be further refined to include additional predicted detail, up to including all atom positions.

Computational methods usually produce lower quality structures than experimental methods, and the models produced by computational methods are often called "inexact models." In contrast, the present methods provide a mechanism for generating precise three-dimensional structure of an mPGES-1 synthase molecule using various forms of information. In the present methods structural motifs from a query polypeptide can be compared to similar motifs in a homologous template polypeptide. The comparison can be repeatedly refined until a final conformation set is obtained. Throughout the refinement process, atomic positions of atoms in the query polypeptide can be repeatedly compared to those of the template polypeptide. The differences can be quantified via a measure called "root mean square deviation" (RMSD). A query model having an RMSD of about 2.0 Å or less as compared to a corresponding experimentally determined template structure is considered "high quality". Frequently, predicted query models have an RMSD of about 2.0 Å to about 6.0 Å when compared to one or more experimentally determined template structures, and are called "inexact models." As those in the art will appreciate, RMSDs can also be determined for one or more atomic positions when two or experimental structures have been generated for the same protein.

The term "root mean square deviation" means the square root of the arithmetic mean of the squares of the deviations. It is a way to express the deviation or variation from a trend or object. For purposes of this invention, the "root mean square deviation" defines the variation in the backbone of a template polypeptide from the backbone of a query polypeptide or an active site portion thereof, as defined by the structure coordinates described herein. "Having substantially the same three-dimensional structure" refers to a polypeptide that is characterized by a set of atomic structure coordinates that have a root mean square deviation (RMSD) of less than or equal to about 1.5 Å when superimposed onto the atomic structure coordinates of a template polypeptide when at least about 50% to 100% of the C-alpha atoms of the coordinates are included in the superposition.

Slight variations in structure coordinates can be generated by mathematically manipulating the template polypeptide structure coordinates. For example, the structure coordinates could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional model is considered to be structurally equivalent.

As used herein, the term "model" refers to a representation in a tangible medium of the three-dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, a carbon traces, ribbon diagrams and electron density maps. A variety of such representations of the structural models of the present invention are shown, for example, in the figures. In practice, predicting the three-dimensional structure of a protein can be attempted on various levels, ranging from purely de novo, or "ab initio," approaches to those that incorporate constraints derived from experimental data.

The primary structure of a polypeptide can be defined as the sequence of amino acid residues that comprise the polypeptide. The alpha carbon of each residue form the scaffold upon which the structure of the polypeptide is built. In general, the single bond between an alpha-carbon and its attached R-group provides limited rotational freedom. Collectively, such structural flexibility enables a number of possible conformations to be assumed at a given region within a polypeptide. As discussed in greater detail below, the particular conformation actually assumed depends on thermodynamic considerations, with the lowest energy conformation being preferred.

In addition to primary structure, proteins also have secondary, tertiary, and, in multi-subunit proteins, quaternary structure. "Secondary structure" refers to local conformation of the polypeptide chain, with reference to the covalently linked atoms of the peptide bonds and alpha-carbon linkages that string the amino acid residues of the protein together. Side chain groups are not typically included in such descriptions. Representative examples of secondary structures include alpha-helices, parallel and anti-parallel beta structures, and structural motifs such as helix-turn-helix, the leucine zipper, the zinc finger, the beta-barrel, and the immunoglobulin fold. Movement of such domains relative to each other often relates to biological function and, in proteins having more than one function, different binding or effector sites can be located in different domains.

"Tertiary structure" concerns the overall three-dimensional structure of a protein, including the spatial relationships of amino acid residue side chains and the geometric relationship of different regions of the protein. "Quaternary structure" relates to the structure and non-covalent association of different polypeptide subunits in a multisubunit protein, such as a trimer.

Modulators of mPGES-1 Activity

As described above, molecular modeling involves the use of computational methods, preferably computer assisted methods, to build realistic models of query polypeptides that are identifiably related in sequence to a template polypeptide having a known crystal structure. The present invention also includes the use of molecular and computer modeling techniques to design and select ligands, such as small molecule agonists or antagonists or other compounds that interact with mPGES-1 molecules. The methods utilized in ligand modeling range from molecular graphics (i.e., three-dimensional representations) to computational chemistry (i.e., calculations of the physical and chemical properties) to make predictions about the binding of ligands or activities of ligands; to design new ligands; and to predict novel molecules, including ligands such as compounds that inhibit the activity of a synthase, such a mPGES-1.

According to the present invention, a "cognate ligand" of a mPGES-1 protein is any protein that interacts with or more particularly, binds to, a mPGES-1 protein in nature (e.g., under any normal, natural, or physiological conditions in vitro or in vivo). As such, the term "cognate" is intended to refer to the relationship in nature between mPGES-1 and other ligands. The term ligand is intended to generically or generally refer to any ligand, binding partner, corepressor, substrate (such terms being capable of use interchangeably) or other protein or compound with which the SBD of mPGES-1 interacts. As such, the term implies any interaction relationship between mPGES-1 and another compound.

The structures used to perform the above-described method have been described in detail above and in the Examples section, and include any structural homologues of proteins described herein. According to the present invention, the phrase "models that define the three dimensional structure" is defined as any means of obtaining, providing, supplying, accessing, displaying, retrieving, or otherwise making available the models defining any three dimensional structures as described herein. For example, the step of providing can include, but is not limited to, accessing the structure from a database or other source; importing the structure into a computer or other database; displaying the model of the structure in any manner, such as on a computer, on paper, etc.; and determining the three dimensional structure described by the present invention de novo using the guidance provided herein.

Methods of structure based identification of compounds of the present invention include identifying a candidate compound for interacting with an SBD in mPGES-1, represented by the structure model, by performing structure based drug design with the model of the structure. According to the present invention, the step of "identifying" can refer to any screening process, modeling process, design process, or other process by which a compound can be selected as useful for binding or inhibiting the activity of protein or complex according to the present invention. Methods of structure-based identification of compounds are described in detail throughout the specification.

Structure based identification of compounds (e.g., structure based drug design, structure based compound screening, or structure based structure modeling) refers to the prediction or design of a conformation of a peptide, polypeptide, protein, or to the prediction or design of a conformational interaction between such protein, peptide or polypeptide, and a candidate compound, by using the three dimensional structure of the peptide, polypeptide or protein. Typically, structure based identification of compounds is performed with a computer (e.g., computer-assisted drug design, screening or modeling). For example, generally, for a protein to effectively interact with (e.g., bind to) a compound, it is necessary that the three dimensional structure of the compound to assume a compatible conformation that allows the compound to bind to the protein in such a manner that a desired result is obtained upon binding. Knowledge of the three dimensional structures of the components of the complexes described herein in the conformation in which they bind to one another enables a skilled artisan to design a compound having such compatible conformation, or to select such a compound from available libraries of compounds and/or structures thereof. For example, knowledge of the three dimensional structure of the substrate binding domain of mPGES-1 enables one of skill in the art to design or select a compound structure that is predicted to bind to the SBD of mPGES-1 at that site and result in, for example, inhibition of the binding of mPGES-1 to its natural ligand. Similarly, one can design or select (identify) a compound that has the opposite, or stimulatory effect on the complex components.

Suitable structures and models useful for structure based drug design are disclosed herein. Preferred target structures, such as the mPGES-1 substrate binding domain or mPGES-1 trimer, include any representation of the structure produced by any modeling method disclosed herein.

According to the present invention, the step of identifying, selecting or designing a compound for testing in a method of structure based identification of the present invention can include creating a new chemical compound structure or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. Chemical compounds can generally include any peptide, oligonucleotide, carbohydrate and/or synthetic organic molecule. A preferred step of designing comprises computational screening of one or more databases of compounds in which the three-dimensional structure of the compound is known and is interacted (e.g., docked, aligned, matched, interfaced) with the three dimensional of a mPGES-1 molecule provided herein by computer (e.g. as described by Humblet and Dunbar, Animal Reports in Medicinal Chemistry, vol. 28, pp. 275-283, 1993, M Venuti, ed., Academic Press). The compound itself, if identified as a suitable candidate by the method of the invention, can be synthesized and tested directly with one or more of the components of an mPGES-1 molecule, or a molecule-ligand complex, for example, in a biological assay. Methods to synthesize suitable chemical or protein-based compounds are known to those of skill in the art and depend upon the structure of the chemical being synthesized. Methods to evaluate the bioactivity of the synthesized compound depend upon the bioactivity of the compound (e.g., inhibitory or stimulatory) and are discussed herein.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies.

In the present method of structure based identification of compounds, it is not necessary to align the structure of a candidate chemical compound (i.e., a chemical compound being analyzed in, for example, a computational screening method of the present invention) to each residue in a target site (target sites will be discussed in detail below). Suitable candidate chemical compounds can align to a subset of residues described for a target site. For example, a subset of residues can include amino acid residues Q36, R110, T114, Y130, and Q134, positioned in the PGH2-binding site of an mPGES-1 molecule. Preferably, a candidate chemical compound comprises a conformation that promotes the formation of covalent or non-covalent cross-linking between the target site and the candidate chemical compound. In one aspect, a candidate chemical compound binds to a surface adjacent to a target site to provide an additional site of interaction in a complex. When designing an antagonist (e.g., a chemical compound that inhibits the biological activity of a mPGES-1 molecule), for example, the antagonist should bind with sufficient affinity to the target binding site or substantially prohibit a ligand (e.g., a molecule that specifically binds to the substrate binding domain) from binding to a target site. It will be appreciated by one of skill in the art that it is not necessary that the complementarity between a candidate chemical compound and a target site extend over all residues specified here in order to inhibit or promote binding of a ligand.

One embodiment of the present invention for structure based drug design comprises identifying a compound (e.g., a chemical compound) that complements the shape of a component of an mPGES-1 molecule-PGES-1 substrate complex, including a portion of mPGES-1 (including, but not limited to, an mPGES-1 trimer. Such method is referred to herein as a "geometric approach". In a geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., J. Mol. Biol., 1982, 161:269-288, which is incorporated by this reference in its entirety. The algorithm for chemical compound design can be implemented using the software program DOCK Package, Version 1.0 (available from the Regents of the University of California). Pursuant to the Kuntz algorithm, the shape of the cavity or groove on the surface of a structure at a binding site or interface is defined as a series of overlapping spheres of different radii. One or more extant databases of crystallographic data (e.g., the Cambridge Structural Database System maintained by University Chemical Laboratory, Cambridge University, Lensfield Road, Cambridge CB2 1EW, U.K.) or the Protein Data Bank maintained by Brookhaven National Laboratory, is then searched for chemical compounds that approximate the shape thus defined. Chemical compounds identified by the geometric approach can be modified to satisfy criteria associated with chemical complementarity, such as hydrogen bonding, ionic interactions or Van der Waals interactions.

Another embodiment provides for structure based identification of compounds comprises determining the interaction of chemical groups ("probes") with an active site at sample positions within and around a binding site or interface, resulting in an array of energy values from which three dimensional contour surfaces at selected energy levels can be generated. This method is referred to herein as a "chemical-probe approach." The chemical-probe approach to the design of a chemical compound of the present invention is described by, for example, Goodford, J. Med. Chem., 1985, 28:849-857, which is incorporated by this reference herein in its entirety, and is implemented using an appropriate software package, including for example, GRID (available from Molecular Discovery Ltd., Oxford OX2 9LL, U.K.). The chemical prerequisites for a site-complementing molecule can be identified at the outset, by probing the substrate binding domain (SBD) of an mPGES-1 molecule with different chemical probes, e.g., water, a methyl group, amine nitrogen, carboxyl oxygen and/or a hydroxyl. Preferred sites for interaction between an active site and a probe are determined. Putative complementary chemical compounds can be generated using the resulting three dimensional patterns of such sites.

According to the present invention, suitable candidate compounds to test using the method of the present invention include proteins, peptides or other organic molecules, and inorganic molecules. Suitable organic molecules include small organic molecules. Peptides refer to small molecular weight compounds yielding two or more amino acids upon hydrolysis. A polypeptide is comprised of two or more peptides. As used herein, a protein is comprised of one or more polypeptides. Preferred therapeutic compounds to design include peptides composed of "L" and/or "D" amino acids that are configured as normal or retroinverso peptides, peptidomimetic compounds, small organic molecules, or homo- or hetero-polymers thereof, in linear or branched configurations. Suitable compounds for design or identification are described in detail below.

A compound that is identified by the method of the present invention can originate from a compound having chemical and/or stereochemical complementarity with a site on one or more components of a SBD of a mPGES-1 molecule as described herein. Such complementarity is characteristic of a compound that matches the surface of the protein(s) either in shape or in distribution of chemical groups and binds to protein(s) to regulate (e.g., by inhibition or stimulation/enhancement) binding of a mPGES-1 molecule to one or more of its cognate ligands, for example, or to otherwise modulate the biological activity of mPGES-1.

The following general sites of amino acid residues Q36, R110, T114, Y130, and Q134, positioned in the PGH2-binding site are targets for structure based drug design or identification of candidate compounds and lead compounds (also referred to herein as target sites or active sites), although other sites may become apparent to those of skill in the art based on the three-dimensional structures provided herein. Although many of the sites described below are illustrated with respect to the specific amino acid sequence of a particular mPGES-1 molecule because the tertiary structures are predicted to be highly similar in homologous target sites on other highly related proteins and complexes (e.g., the homologous protein in different mammalian species; different mPGES-1 proteins that are structurally related) it is to be understood that the description of the target sites is intended to encompass all other such homologues of the exemplified sequences and structures. One of skill in the art can readily extrapolate the amino acid residues within a sequence described herein to the corresponding amino acid residues in a highly related sequence simply by aligning the related sequences. More specifically, one of skill in the art can readily determine whether a given sequence aligns with another sequence, as well as identify conserved regions of sequence identity or homology within sequences, by using any of a number of software programs that are publicly available. For example, one can use BLOCKS (GIBBS) and MAST (Henikoff et al., Gene, 1995, 163:17-26; Henikoff et al., Genomics 1994, 19:97-107), typically using standard manufacturer defaults.

Exemplary target sites include, but are not limited to: (1) amino acid residues Q36, R110, T114, Y130, and Q134, positioned in the PGH2-binding site; (2) amino acid residue Y130 in proximity to the peroxy head of PGH2 and the —SH group of GSH in the binding site; around residue Y130 of mPGES-1, reflecting the distinct role of Y130 residue; (3) the mPGES-1-catalyzed reaction of PGH2 can be initialized by the electrophilic attack of the —SH group of GSH at the peroxy oxygen of PGH2; and (4) amino acid residues R110, T114, and Q36 contact the carboxyl tail of PGH2. These target sites are described in detail in the Examples and the Figures. Combinations of any of these general sites are also suitable target sites. These sites are generally referenced with regard to the tertiary structure of the sites. Even if some of such sites were generally known or hypothesized to be important sites prior to the present invention, the present invention actually defines the sites in three dimensions and confirms or newly identifies residues that are important targets that could not be confirmed or identified prior to the present invention. The use of any of these target sites as a three dimensional structure is novel and encompassed by the present invention. Many of these target sites are further described below and illustrated in the Figures and Examples of the invention.

The potential, predicted inhibitory agonist, inhibitory antagonist, or binding effect of a ligand or other compound on mPGES-1 molecules, such as the substrate binding site and/or mPGES-1 trimers, may be analyzed prior to its actual synthesis and testing by the use of computer modeling techniques. If the theoretical structure of the given compound suggests insufficient interaction and association between it and the mPGES-1 molecules, synthesis and testing of the compound may be obviated. However, if computer modeling indicates a strong interaction, the molecule may then be synthesized and tested for its ability to interact with mPGES-1 molecules. In this manner, synthesis of inoperative compounds may be avoided. In some cases, inactive compounds are synthesized predicted on modeling and then tested to develop a SAR (structure-activity relationship) for compounds interacting with a specific region of mPGES-1 molecules, such as the substrate binding site, or a multimer of mPGES-1, such as an mPGES-1 trimer.

One skilled in the art may use one of several methods to screen chemical entities fragments, compounds, or agents for their ability to associate with mPGES-1 molecules. This process may begin by visual inspection of, for example, the active site based on the atomic coordinates of the polypeptide or the polypeptide complexed with a ligand. Selected chemical entities, compounds, or agents may then be positioned in a variety of orientations, or docked within an individual binding pocket of mPGES-1 molecules. Docking may be accomplished using software-such as Quanta and Sybyl, followed by energy minimization and molecular dynamics with standard molecular mechanics forcefields, such as CHARMM and AMBER.

The use of software such as GRID, a program that determines probable interaction sites between probes with various functional group characteristics and the macromolecular surface, is used to analyze the surface sites to determine structures of similar inhibiting proteins or compounds. The GRID calculations, with suitable inhibiting groups on molecules (e.g., protonated primary amines) as the probe, are used to identify potential hotspots around accessible positions at suitable energy contour levels. The program DOCK may be used to analyze an active site or ligand binding site and suggest ligands with complementary steric properties. See also, Kellenberger et al., Proteins, 2004, 54:671-80; Oldfield, 2003, Methods Enzymol. 374:271-300; Richardson et al., 2003, Methods Enzymol. 374:385-412; Terwilliger, 2003, Acta Crystallogr D Biol Crystallogr. 59:1174-82; Toerger and Sacchettini, 2003, Methods Enzymol. 374:244-70; von Grotthuss et al., 2004, Science 304:1597-9; Rajakiannan et al., 2004, J Synchrotron Radiat. 11:358-62; Claude et al., 2004, Nucleic Acids Res. 32:W606-9; Suhre and Sanejouand, 2004, Nucleic Acids Res. 32:W610-4.

Once a compound that associates with mPGES-1 molecules has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation may be avoided. Such substituted chemical compounds may then be analyzed for efficiency of fit to a mPGES-1 molecules by the same computer methods described in detail above.

Data Storage and Retrieval

The invention encompasses machine-readable media embedded with the three-dimensional structure of the model described herein, or with portions thereof. As used herein, "machine-readable medium" refers to any medium that can be read and accessed directly by a computer or scanner. Such media include, but are not limited to: magnetic storage media, such as floppy discs, hard disc storage medium and magnetic tape; optical storage media such as optical discs or CD-ROM; electrical storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with an OCR.

A variety of data storage structures are available to a skilled artisan for creating a computer readable medium having recorded thereon the atomic structure coordinates of the invention or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, Protein Data Bank ("PDB") format (Research Collaboratory for Structural Bioinformatics; Cambridge Crystallographic Data Centre format; Structure-data ("SD") file format (MDL Information Systems, Inc.; Dalby et al., J. Chem. Inf. Comp. Sci., 1992, 32:244-255), and line-notation, e.g., as used in SMILES (Weininger, J. Chem. Inf. Comp. Sci., 1988, 28:31-36). Methods of converting between various formats read by different computer software will be readily apparent to those of skill in the art, e.g., BABEL (v. 1.06, Walters & Stahl, ©1992, 1993, 1994). All format representations of the polypeptide coordinates described herein, or portions thereof, are contemplated by the present invention. By providing computer readable medium having stored thereon the atomic coordinates of the invention, one of skill in the art can routinely access the atomic coordinates of the invention, or portions thereof, and related information for use in modeling and design programs, described in detail below.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, is also useful for representing a three-dimensional molecular structure.

Accordingly, also provided herein is a machine-readable data storage medium including a data storage material encoded with machine readable data which, when using a machine programmed with instructions for using the data, displays a graphical three-dimensional representation of a mPGES-1 molecule.

Structure information, typically in the form of the atomic structure coordinates, can be used in a variety of computational or computer-based methods to, for example, design, screen for and/or identify compounds that bind the crystallized polypeptide or a portion or fragment thereof, or to intelligently design mutants that have altered biological properties, and the like. Such modeling includes, but is not limited to, drawing pictures of the actual structures, building physical models of the actual structures, and determining the structures of related subunits and/ligand and subunit/ligand complexes using the coordinates. Such molecular modeling can utilize known X-ray diffraction molecular modeling algorithms or molecular modeling software to generate atomic coordinates corresponding to the three-dimensional structure of an mPGES-1 molecule.

The information can be included in an information storage, manipulation and retrieval system, such as a computer system. Such a system can include a representation of the three-dimensional structure of an mPGES-1 molecule of the invention, such as a monomer, substrate binding domain or trimer. Generally such a system includes a user interface to view the representation.

Also provided herein are methods for conducting a biotechnology business. The methods include identifying one or more candidate compounds for regulation of interactions of mPGES-1 with its cognate ligands by a method described herein. The business method further includes generating a machine-readable medium, or data signal embodied in a carrier wave, embedded with information that corresponds to the three-dimensional structural representation of the candidate compound and providing the medium or data signal to an end user.

The following examples are provided to illustrate the practice of preferred embodiments of the instant invention, and in no way limit the scope of the invention.

EXAMPLES

In order to understand the molecular mechanism of the substrate binding, an "ab initio" structure prediction approach has been developed in the present study to build a three-dimensional model of the substrate-binding domain (SBD) of mPGES-1 by making use of the structural information available for both mPGES-1 and MGST1 of the MAPEG superfamily. Based on the three-dimensional model of the SBD, key residues that are crucial for the substrate binding have been identified through further structural analysis and molecular docking. Molecular docking is generally defined as the relative positioning of two or more interacting bodies. Such a positioning can be done by means of complex algorithms to match physical properties of the multiple bodies or by a simple procedure such as visual analysis. Accurate and intuitive docking, with easy and accessible information of the docking process, is an important process in the development of pharmaceuticals and novel materials as well as in understanding the properties of existing systems.

Site-directed mutagenesis and catalytic activity assays have been performed to validate the predicted three-dimensional SBD model of the wild-type mPGES-1 and its mutants. The overall agreement between the computational and experimental results demonstrates some important structural features of the SBD of mPGES-1 and it's binding with the substrates, providing a basis for structure-based design of compounds that interact with the SBD.

"Ab initio" Structure Prediction: The sequence alignment between MGST-1 and mPGES-1 (see FIG. 1) was generated by using ClusterW with the Blosum scoring function. The best alignment was selected according to not only the alignment score, but also the reciprocal position of the conserved residues. These included the conserved FANPED motif at amino acid positions #44 to #49, VERXXRAH motif from position #65 to #72 and R110. There was a gap of four residues from #55 to #58. The total homology is 73%, with the sequence identity of 38.8%. The membrane-spanning regions were defined based on the analysis of amino acids distribution and the homology with MGST1. The locations of substrates PGH2 and GSH in the SBD of mPGES-1 were thought to be similar to the corresponding locations of the substrates in the SBD of MGST1 revealed by the electron density map of MGST1 (Schmidt-Krey et al., EMBO J., 19:6311-6316; Holm et al., Biochem. Biophys. Acta, 1594: 276-285) Considering the low-resolution quaternary structure of mPGES-1, the "ab initio" rationale (see FIG. 10) began with the construction of topological model in which each helix was represented by C-alpha atoms, according to the structural parameters derived from the reported two-dimensional and three-dimensional electron projection maps of mPGES-121 and MGST1 and shown in Table 1 below:

| Helix | A | B | C | D |
| --- | --- | --- | --- | --- |
| Helix center (x,y plane) | 11.0Å, 16.0Å | 9.0Å, 2.0Å | 0.0Å, 0.0Å | 19.0Å, 10.0Å |
| Tilt angle(θ) | 27.0°~37.0° | 12.0°~20.0° | 12.0°~22.0° | 18.0°~18.0° |
| Helix-between distance | A-C: 19.4Å | B-C: 9.2Å | | D-C: 21.5Å |
| Helix arrangement | | Anti-clockwise | | |
| Membrane thickness | | 26.0 Å | | |
| Kink of helix C toward helix A | | 3.0 Å | | |
| Kink point to the C-terminal of helix C | | 11.0 Å | | |
| Motion along the membrane normal (z axis) | | ±5.0 Å | | |
| Relative rotation of each helix | | ±180.0° | | |
| Self-rotation of each helix | | ±180.0° | | |
| Orientation of hydrophobic residues | | Toward membrane | | |

Here, the considered SBD is composed of alpha-helices A, C, and D from one monomer and alpha-helix B from another neighboring monomer. The orientation of each alpha-helix was explored along three degrees of freedom, including the relative motion along the normal to the membrane, relative rotation among helices, and the helical self-rotation. A set of 144784 candidate topological (C-alpha) structures were generated and subsequently transformed into the corresponding residues of each helix. A set of criteria (Table 1) were used to screen the candidate structures and only 1934 candidate structures were kept for further consideration. The structures of these 1934 candidates were then fully optimized by performing energy minimization using the Sander module of Amber7.0 program suite. Initially, the loop between alpha-helices C and D was not considered. The energy minimization was carried out by using a non-bonded cutoff of 10 Å and conjugate gradient method, first with fixed backbone for 500 steps and then with constrained side chains for 300 steps. This was followed by energy minimization on the whole molecule for 1000 steps. Further energy minimization was performed after adding the loop between alpha-helices C and D. The energy minimization was continued until the root-mean square deviation (RMSD) of the energy gradient was smaller than 0.001 kcal mol$^{-1}$ Å$^{-1}$. Additional geometric screening was based on the structural compatibility among all the helices, as well as the overall deviation of the C-alpha atoms from the initial positions. This process eventually resulted in a set of 27 candidate structures (conformations) with some structural diversity and closely related low energies. These sets of molecular structures were viewed as the most possible conformations of the SBD of mPGES-1 and were used in further molecular docking tests.

Molecular Docking and Mutational Calculation: The two native substrates PGH2 and GSH were treated as ligands, and were separately docked into the aforementioned 27 candidate structures of the SBD of mPGES-1 by using the AutoDock 3.0.5 program. The atomic charges used for these two ligands were the electrostatic potential (ESP)-fitted charges determined by performing first-principles electronic structure calculations using Gaussian03 program at the HF/6-31G* level. The similar ESP-fitting calculations based on the first-principles electronic structure method were used in previous computational studies of other protein-ligand systems and led to satisfactory binding structures. The molecular docking was performed with a large population of randomly sampled ligand conformations and with random molecular translations using the Lamarkian genetic algorithm (LGA). Through three types of operations in the LGA method, namely selection, mutation, and crossover, the substrate-enzyme matching quality was monitored and improved. On each docking site, the ligand conformation was searched by using the Solis and Wets local search method in order to sample all the possible ligand conformations. Among a series of docking parameters, the size of the grid, in which both the enzyme and the ligand were embedded, was set to be 60 Å×60 Å×60 Å along the x, y, and z directions. This size of grid is large enough to cover all the protein atoms near the docking site, and is also sufficient for calculating the long-range electrostatic interactions between the enzyme and ligand molecules. All the complex candidates were evaluated and ranked in terms of the binding free energies by using the standard energy score function implemented in the docking program and the geometric matching quality. The best complex candidate was selected from the docked structures according to the best geometric matching and the low binding free energy (high binding affinity). As the enzyme structure was kept rigid in the above docking process, the structure of this selected complex candidate was further refined through the energy minimization using the aforementioned Amber7.0 program, leading to the construction of the final complex structure.

Residue-based analysis was carried out for the obtained complex structure. Critical atomic contacts between the substrates and the enzyme were identified and the identified crucial residues binding with PGH2 include Q36, R110, T114, Y130, and Q134. In order to estimate individual contributions from these residues to the binding affinity with PGH2 and to know their possible role in the binding with the second substrate GSH, the substrate-bound SBD structures of five mPGES-1 mutants was further examined: Q36E, R110T, T114V, Y130I, and Q134E. The initial SBD structures of these mutants were generated based on the finally refined SBD structure of the wild-type by using the InsightII program (version 2002, Accelrys, San Diego, Calif.). The initial SBD structures of the substrate-bound mPGES-1 mutants were energy-minimized by using the same method as used for the substrate-bound wild-type mPGES-1. The substrate binding free energy (ΔG) with each mutant was calculated in the same way as we did for the binding with the wild-type enzyme. All the computations were performed on a supercomputer (Superdome) at University of Kentucky Center for Computational Sciences and on SGI Fuel workstations and a 34-processors IBM x335 Linux cluster.

Vector, Membrane, and Cloning of mPGES-1: PQE40 expression vector, E. coli M15 and QIAprep Spin Plasmid miniprep Kit were from QIAgene. Restriction endonucleases were from New England BioLabs. The pfu polymerase was from Stratagene. Nickel-HRP was from Kirkegaard & Perry Laboratories (Gaithersburg, Mass.), polyvinylidene fluoride (PVDF) membrane was from Millipore Corp. ECL western blotting detection system RPN 2132 was from Amersham Life science. Oligonucleotide primers were synthesized by MWG biotech. PGH2 and PGE2 were purchased from Cayman chemicals. Other chemicals were from Sigma. The sequence of mPGES-1 was extracted from Genebank (access No. AF27740). The specific oligonucleotide primers to full length of mPGES-1 were synthesized to incorporate restriction sites (BamHI and HindIII) into the 5' and 3' ends of the products. PCR was performed with 2 units Taq polymerase, 1 µl human placenta cDNA library. The PCR product was subcloned into *E. coli* expression vector plasmid PQE40 at BamH I and Hind III sites, which would express histidine X6 tagged mPGES-1. The ligated plasmids were transformed into XLI-Blue competent cells with the insertion confirmed by DNA sequencing.

Site-Directed Mutagenesis of mPGES-1: The internal primers were designed to contain sense and antisense mutagenic factors with mismatched codons in the wild-type sequence. All the mutations of mPGES-1 cDNA were performed by quick change site-directed mutagenesis method. The sequences of oligonucleotides used for mutagenesis were:

```
Q36E:
                                        (SEQ ID NO: 1)
5'-GTGGCCATCATCACGGGCGAAGTGAGGCTGCGGAAGAAG,
and (SEQ ID NO: 2)
5'-CTTCTTCCGCAGCCTCACTTCGCCCGTGATGATGGCCAC;

R110T:
                                        (SEQ ID NO: 3)
5'-CTGGTCTTCCTCGTGGGCACTGTGGCACACACCGTGGCC,
and (SEQ ID NO: 4)
5'-GGCCACGGTGTGTGCCACAGTGCCCACGAGGAAGACCAG;

T114V:
                                        (SEQ ID NO: 5)
5'-GTGGGCCGTGTGGCACACGTCGTGGCCTACCTGGGGAAG,
and (SEQ ID NO: 6)
5'-CTTCCCCAGGTAGGCCACGACGTGTGCCACACGGCCCAC;

Y130I:
                                        (SEQ ID NO: 7)
5'-CCCATCCGCTCCGTGACCATCACCCTGGCCCAGCTCCCC,
and (SEQ ID NO: 8)
5'-GGGGAGCTGGGCCAGGGTGATGGTCACGGAGCGGATGGG;

Q134E:
                                        (SEQ ID NO: 9)
5'-GTGACCTACACCCTGGCCGAGCTCCCCTGCGCCTCCATG,
and (SEQ ID NO: 10)
5'-CATGGAGGCGCAGGGGAGCTCGGCCAGGGTGTAGGTCAC;
``` where the underlines indicate the bases that were changed. Pfu DNA polymerase was used for PCR. The PCR products were treated with DpnI endonuclease to digest the parental DNA template. All the mutant plasmids were transformed into XLI-Blue cells to amplify DNA. The DNA sequences of mutants were confirmed by sequencing.

Expression and Preparation for the Membrane Fraction of mPGES-1 and its Mutants in *E. coli*: The wild-type mPGES-1 and its mutant plasmids from XLI-Blue were transformed into M15 *E. coli* cells. Cells were grown in 500 ml TB media containing 100 µg/ml ampicillin and 25 µg/ml kanamycin at 37° C. with shaking at 270 rpm until OD reached 0.8. IPTG was added to a final concentration of 2 mM and cells were allowed to grow for additional 3 hours at 37° C. Cells were then harvested by centrifugation at 5000 g for 15 min at 4° C. The cell pellet was re-suspended in 15 mM Tris-HCl pH 8.0 containing 0.25 M sucrose, 0.1 mM EDTA and 1 mM reduced form glutathione. The cells were broken by sonication, and then the cell lysate was cleared by centrifugation at 12,500 g for 10 min. The supernatant then was centrifugated at 250,000 g 4° C. for 1 hour and the membrane pellet were re-suspended in PPGEG buffer (10 mM potassium phosphate, pH 7.0, 20% glycerol, 0.1 mM EDTA and 1 mM reduced form glutathione). Total protein concentration of the membrane fraction was determined by coomassie protein assay according to the manufacture's instruction (Bio-Rad) with BSA as a standard.

SDS-PAGE and Western Blotting: The *E. coli* membranes (50 µg) expressing the His-tagged wild-type and mutant mPGES-1 were subjected to SDS-PAGE on 15% polyacrylamide gel. The proteins were then electrophoretically transferred onto PVDF membranes. The membrane was blocked with 5% nonfat milk in TBS (30 mM Tris-HCl, pH 7.4 containing 120 mM NaCl) at room temperature for 1 hour. After incubation 2 hours at room temperature with Nickel-HRP (1:500) in 5% nonfat milk in TBS, the membrane was washed 3 times with TBS containing 0.1% Tween 20. The immunoreactive bands were detected with ECL plus western blotting detection system.

Activity Assay for Wild-type mPGES-1 and Its Mutants: Assays for mPGES-1 activity were performed on ice in 1.5 ml microfuge tubes using PGH2 as substrate. The reaction mixture (100 µl) contained: 100 mM sodium phosphate, pH 7.2, 2.5 mM GSH and enzyme preparation. The reaction was initiated by the addition of 15 µM PGH2 from 20-fold concentrated stock solution in dry ethanol. After 8 min of incubation on ice, the reaction was quenched by the addition of 100 µl (2 mg/ml) SnCl2 which rapidly reduced un-reacted PGH2 to PGF2α. The non-enzymatic conversion of PGH2 to PGE2 was performed using PPGEG buffer devoid of enzyme. The reaction contents were 1:2500 diluted, from which 50 µl aliquot was used for quantification of PDE2 concentration by EIA assay. The mPGES-1 activity was calculated using enzymatic conversion of PGH2 to PGE2 from total conversion subtracted by non-enzymatic conversion. When the saturation kinetics for PGH2 was determined, the activity was assayed with a fixed concentration of 2.5 mM GSH and 1-500 µM PGH2. The KM values of wild-type mPGES-1 and its mutants were calculated by using the GraphPad Prism 4.01 program.

Figure 2:
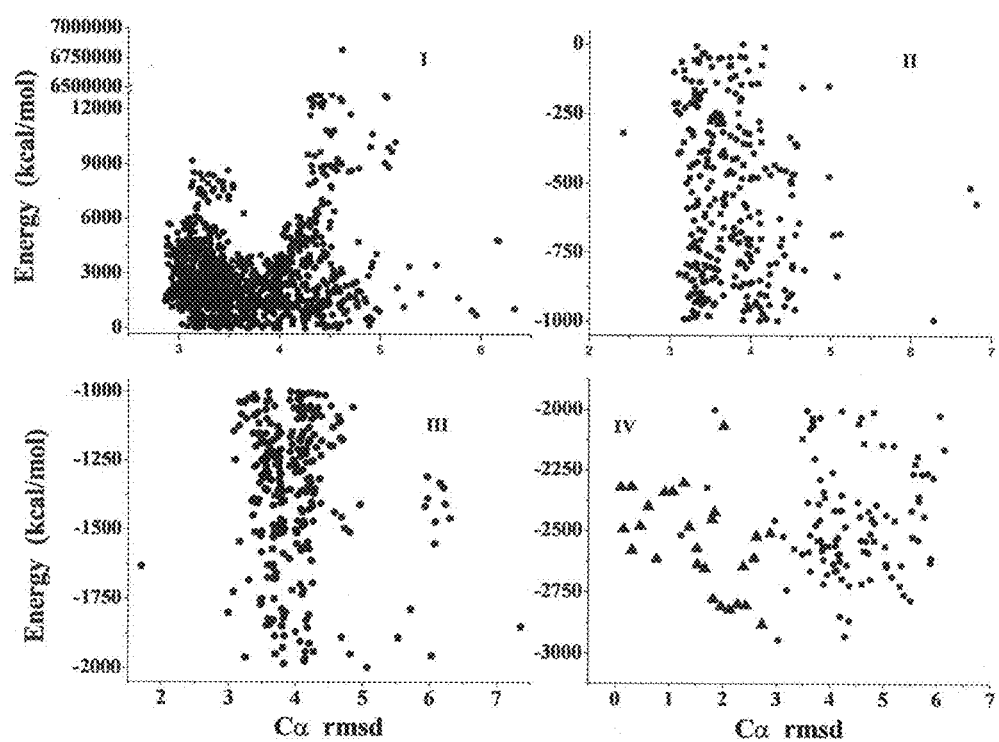
FIG. 2 depicts the second set of 1934 conformations clustered into four groups based on their energies and C-alpha root mean square deviation (RMSD) values relative to the initial topological model. Group I (1232 candidates) was discarded due to their positive potential energies, whereas groups II (285 candidates), III (286 candidates) and IV (131 candidates) were used to derive the final set of 27 candidates. The selected 27 candidates are shown as triangles.
Figure 3:
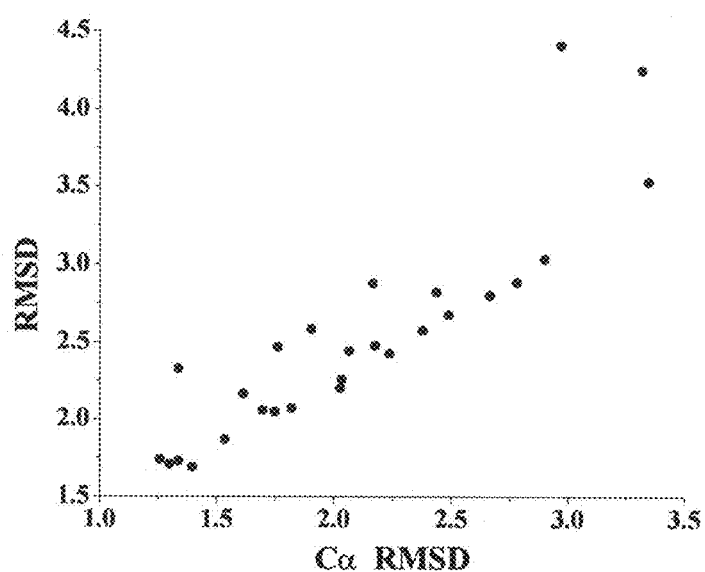
FIG. 3 depicts conformational root-mean square deviation (RMSD) from the initial topological model for the finally selected 27 candidates of the SBD model of mPGES-1.

Results: Structural Models of the SBD of mPGES-1: The amino acid sequence alignment of mPGES-1 with MGST1 (FIG. 1) shows that four regions with high homology (>70%) can be assigned to four alpha-helices. These are alpha-helix A from sequence position #11 to #38, alpha-helix B from #78 to #93, alpha-helix C from #96 to #114, and alpha-helix D from #126 to #147. The longest loop between alpha-helix A and alpha-helix B contains typically conserved motifs. According to the geometric parameters used for the alpha-helices (see Table 1, supra), the explored 144784 conformations derived from the initial topological model are screened down to 1934 candidate conformations. After the energy minimizations using the Sander module of Amber7.0 program, these 1934 candidates were clustered into four groups as shown in FIG. 2. The 1232 candidates in the first group have positive energies, indicating that these 1232 candidate conformations are energetically unfavorable and should be excluded. The energies calculated for the other groups of candidates are negative and become lower and lower from group II to group IV (see FIG. 2), showing the significant improvement of the positions of the side chains. This funnel-like adaptation of the four alpha-helices packing clearly shows both the energetic and geometric aspects dominating the formation of the final reasonable conformations of mPGES-1. Such folding-mimic process (see FIG. 10) also helps to reduce the redundancy of the helix orientations. More strict geometric checking and evaluation of the root-mean-square-deviation (RMSD) of the C-alpha positions from those in the initial topological model help us obtain eventual 27 best candidate conformations selected from group IV (see FIG. 2). Although some of the other candidate structures also had small RMSD values and lower energies, those candidate structures were not selected because the helix packing was not as good as the selected 27 ones. Further, the helix packing was re-examined more strictly according to the geometric criteria (see Table 1, supra) and was finely tuned for the selected 27 candidates. Each of the finely tuned 27 candidate structures was energy-minimized again by using the Sander module of Amber7.0 program until the energy gradient criterion of 0.001 kcal mol$^{-1}$ Å$^{-1}$ was achieved. The finally energy-minimized 27 candidate conformations with low energies and small RMSD values (FIG. 3) can be considered as the most possible conformations of the SBD of mPGES-1.

Complex Model for mPGES-1 Binding with PGH2 and GSH: The first test on the 27 structural models of the SBD of mPGES-1 was performed for their binding with substrates PGH2 and GSH, through molecular docking using both the binding site searching and interaction energy scoring. Each of the 27 structures was used to perform molecular docking, with PGH2 and GSH separately. The calculated binding free energies of PGH2 with the SBD of mPGES-1 range from −4.1 to −8.3 kcal/mol. The corresponding values of the dissociation constant ($K_d$) fall between 995 μM to 0.768 μM. The range of predicted $K_d$ values covers the reported experimental values (~28, ~14, and ~160 μM) of the Michaelis-Menten constant ($K_M$). We note that $K_d \neq K_M$ in theory. Nevertheless, $K_d \approx K_M$ under the widely used rapid-equilibration assumption which assumes that the dissociation of the enzyme-substrate complex is much faster than the corresponding catalytic reaction. The catalytic reaction is characterized by the catalytic rate constant ($k_{cat}$). Based on the reported low $k_{cat}$ values (1.8 to 50 S$^{-1}$) for mPGES-1, $K_d \approx K_M$ in subsequent calculations and discussions. The finally selected complex model of mPGES-1 binding with both PGH2 and GSH substrates was the most satisfactory one with optimal geometric matching (see FIG. 4A) compared to the other complex candidates. The binding free energy (ΔG) calculated for the final complex model is −7.8 kcal/mol for PGH2 and −6.0 kcal/mol for GSH, respectively. Assuming $K_d \approx K_M$, the energetic results calculated for the final complex model predict a $K_M$ value of 2.1 μM for PGH2 and a $K_M$ value of 41.3 μM for GSH.

Based on the predicted complex model shown in FIG. 4B, substrate PGH2 stays in a pocket formed by alpha-helices A, C, and D, with the two tails of PGH2 buried deeply. PGH2 has contacts with both hydrophilic and hydrophobic residues of mPGES-1. The most important interactions are around the carboxyl group on one tail of PGH2, which is surrounded by the polar side chain of Q36, positively charged side chain of R110, and side chain of T114 from alpha-helix C. The binding of these residues with PGH2 is associated with a network of electrostatic and hydrogen bonding interactions. Such an interacting mode is consistent with the reported experimental finding that R110S mutant of mPGES-1 completely lost the catalytic activity. The hydroxyl group on the other tail of PGH2 interacts with side chain of Q134 through possible hydrogen bonding, and this hydrophobic tail is surrounded by side chains of V29, V30, I33, and V37, further strengthening the binding affinity of PGH2 with mPGES-1. As seen in the complex model, the two oxygen atoms forming the peroxy bridge of PGH2 also interact with the —SH group of GSH through hydrogen bonding. The head of the PGH2 molecule is close to the aromatic side chain of Y130 and is covered by hydrophobic part of the side chain of K120.

For the binding of GSH with the SBD of mPGES-1, as shown in FIG. 4C, GSH is bound in a site nearby PGH2 under the loop between alpha-helices C and D. Compared to the location of PGH2, GSH is closer to surface of the protein. Based upon this model, another alpha-helix C in a neighboring monomer could also be involved in the binding with GSH. The molecular docking with GSH was also guided by the insights obtained from the reported two-dimensional and three-dimensional electro-density maps of mPGES-1 and MGST1. Useful features of the GSH binding still can be derived from the current model. As shown in FIG. 4C, GSH is surrounded by Y80, L118, K120, L121, P124, R126, and Y130, and it is close to PGH2. Besides the thiol (—SH) group of GSH interacts with PGH2, the carboxyl group on the Gly-end of GSH interacts with positively charged side chain of R126. Another carboxyl group on the gamma-Glu-end of GSH points toward the backbone of K120 and L121. The packing of the —SH group of GSH and the head of PGH2 with the aromatic side chain of Y130 implies a possibly important role of Y130 in the catalytic function of mPGES-1.

PGH2 Binding with mPGES-1 Mutants: Based on the modeled SBD structure of mPGES-1 and the modeled binding structures with substrates, five key residues (i.e. Q36, R110, T114, Y130, and Q134) involved in the PGH2-binding site were selected for mutational studies in order to further test the predicted SBD model of mPGES-1. According to the three-dimensional model of the substrate binding discussed above, the enzyme binding with substrate PGH2 should be weakened by such mutations as Q36E, R110T, T114V, Y130I, and Q134E. The binding affinities were estimated for the mutants of mPGES-1 by using the same method as used for the wild-type enzyme. The calculated results are summarized in Table 2 in comparison with available experimental data:

| Enzyme | Calculated binding | | Experimental $K_M$ (μM) | |
| --- | --- | --- | --- | --- |
| | ΔG (kcal/mol) | $K_d$ (μM) | This work | Previously reported |
| Wild-type | −7.8 | 2.1[b] | 130 | 14 to 160 [a] |
| Q36E | −3.8 | 1600 | ~1610 | |
| Q134E | −4.7 | 359 | ~734 | |

The experimental $K_M$ values reported previously by other groups ([a]) are 28 μM), 14 μM, and 160 μM. The calculated $k_d$ value ([b]) is close to the range of the experimental $K_M$ values (14 to 160 μM).

Membrane Expression of mPGES-1 and Its Mutants: Based on the information of the structure prediction and modeling on substrate binding, five residues in the PGH2-binding site of mPGES-1 were selected for further site-directed mutagenesis studies. The substitutions for these five residues are Q36E, R110T, T114V, Y130I, and Q134E. The wild-type mPGES-1 was cloned from human placenta cDNA library by PCR techniques using specific sense and anti-sense primers of mPGES-1. The wild-type and the five mutants of mPGES-1 were expressed in M15 *E. coli* cells. As the membrane proteins are very toxic to the host *E. coli*, a special strategy was used to produce sufficient amount of expression in order to favor the next activity assay. The best condition for expression was selected as 3 hours at 37° C. The membrane fractions were further analyzed by western blotting using Ni-HRP as a detection system, which is more sensitive and accurate than the traditional analysis system of the primary and secondary antibody. The results demonstrate that all the five mutants were expressed at a level comparable with that of the wild-type enzyme (see FIG. 5).

Enzymatic Activity and Kinetic Data: The wild-type and the mutants of mPGES-1 were assayed for the enzymatic activity in the presence of PGH2 and GSH as substrates and the results are shown in FIG. 6. The R110T mutation was designed to test mainly for its electrostatic and hydrogen bonding interactions with the carboxyl group of PGH2. This mutant retained only 17.8% catalytic activity of the wild-type, not totally abrogated as reported by Murakami et al. (J. Biol. Chem., 2000, 275:32783-32792). The T114V mutant showed 21.3% activity of the wild-type mPGES-1, which is consistent with the computational prediction that the hydroxyl group of T114 side chain is involved in hydrogen bonding with PGH2. The Y130I mutant lost most of the enzymatic activity, indicating that this residue cannot tolerate any amino acid change. This suggests that the role of Y130 in the reaction of PGH2 catalyzed by mPGES-1 is crucial. Q36E and Q134E mutants kept about 40%-50% catalytic activity of the wild-type (FIG. 6), indicating that these two residues (Q36 and Q134) are not as important as the other three residues (R110, T114, and Y130) for the catalytic reaction.

The experimental results are listed in Table 2 and depicted in FIGS. 6 and 7 for comparison with the computational predictions. As seen in FIG. 6, each of the tested mPGES-1 mutants demonstrated a lower catalytic activity compared to the wild-type, which is qualitatively consistent with the predicted enzyme-substrate binding model. Quantitatively, the experimental kinetic constant $K_M$ was determined only for the wild-type mPGES-1 and the Q36E and Q134E mutants, but the catalytic activity of the R110T, T114V, and Y130I mutants is too low for the measurement of kinetic constants. The correlation between the calculated $K_d$ and the measured $K_M$ for these two mutants is represented in FIG. 8. For the wild-type mPGES-1, the experimental $K_M$ value of 130 µM is comparable to the $K_M$ values reported by Tanikawa et al. (28 µM) (Biochem. Biophys. Res. Com., 2002, 291:884-889), Ouellet et al. (14 µM) (Protein Expr. Puri., 2002, 26:489-495), and Thoren et al. (160 µM) (J. Biol. Chem., 2003, 278:22199-22209). The calculated $K_M$ value of 2.1 µM is acceptable, although it is slightly smaller than the experimental range (14 to 160 µM). The binding constant ($K_d$) values predicted for the Q36E and Q134E mutants are in agreement with the experimental $K_M$ values, although the errors of the experimental $K_M$ values determined for these two mutants are expected to be very large because the concentrations of PGH2 used in the experiments (≤500 µM) are not sufficiently high due to the limitation of the solubility of PGH2. The overall qualitative agreement of the calculated results with the experimental data further supports the predicted three-dimensional model of the substrate-enzyme binding as provided herein.

Structural determination of membrane-spanning proteins is still exceedingly difficult by experimental methods such as X-ray diffraction and NMR. As a stimulating drug target, detailed information about the mPGES-1 structure and the relationship with its functions are needed. In the present study, this need is satisfied by performing computational three-dimensional structure predictions of the SBD of mPGES-1 and it's binding with the substrates PGH2 and GSH, followed by wet experimental tests on the enzyme-substrate binding model predicted at atomic level. The three-dimensional model reveals key amino acid residues, including Q36, R110, T114, Y130, and Q134, involved in the PGH2-binding site. This first three-dimensional model provides a mechanism for designing agents that modulate the activity of mPGES-1 by interacting with the SBD described herein.

The current results (see e.g., FIGS. 6 and 7 and Table 2) obtained from the site-directed mutagenesis and enzymatic activity assay have identified two remarkable features of the predicted mPGES-1 binding with the substrates. One is the relative positions of the peroxy head of PGH2 to the —SH group of GSH in the binding site around residue Y130 of mPGES-1, reflecting the distinct role of Y130 residue. Such a mode of the intermolecular interaction clearly explains why the catalytic function of mPGES-1 is GSH-dependent as observed in previous characterization studies on this enzyme. The obtained binding mode also indicates that the mPGES-1-catalyzed reaction of PGH2 can be initialized by the electrophilic attack of the —SH group of GSH at the peroxy oxygen of PGH2. Also provided herein are the contacts between the carboxyl tail of PGH2 and residues R110, T114, and Q36 of mPGES-1. Intermolecular interactions on this subsite reveal the role of residues R110, T114, and Q36 in the binding of mPGSE-1 with PGH2. R110 is conserved not only strictly for the MGST1 subfamily, but also for the whole superfamily of MAPEG (Jakobsson, et al., Protein Sci., 1999, 8:689-692; Jakobsson et al., Am. J. Respir. Crit. Care Med., 1996, 161:S20-S24; Ekstrom et al., Biochem. Biophys. Acta, 2003, 1627:79-84) suggesting a similar binding/catalytic role of this residue for all the members of this superfamily. The hydrogen bonding between the substrate and the subfamily-conserved residue T114 indicates a similar role of this residue for the members of MGST1 subfamily in the binding with the substrate. The indispensable role of the substitutable conserved Y130 demonstrates why mPGES-1 is specific for the reaction of PGH2. Amino acid residues #36 and #134 are not conserved even for the MGST1 subfamily, which is consistent with our observation that the catalytic activity of mPGES-1 did not dramatically decrease when these two residues were mutated.

Accordingly, in one embodiment, the present combined computational modeling and wet experimental tests have led to establishment of a three-dimensional model of the SBD of mPGES-1 and the identification of how mPGES-1 binds with various substrates at the atomic level. Based on the three-dimensional model, further computational modeling and binding free energy calculations were performed to evaluate the substrate binding with Q36E, R110T, T114V, Y130I, and Q134E mutants of mPGES-1, followed by the site-directed mutagenesis and catalytic activity tests. The overall agreement between the calculated and experimental results demonstrates that the predicted three-dimensional model will be valuable in future rational design of potent inhibitors of mPGES-1 for novel inflammation-related therapeutics.

In another embodiment, the present studies also provide three-dimensional models of the mPGES-1 trimer. The computational modeling of the mPGES-1 trimer models was based on the use of the previously constructed three-dimensional model of the SBD (see data provided supra) and the use of the X-ray crystal structure of cytochrome c protein.

The principle behind homology modeling is the assumption that structure is more highly conserved than sequence. This assumes an evolutionary process called divergent evolution. Thus, the deduced structure of the MGST-1 trimer observed in the three-dimensional projection map (Schmidt-Krey et al., EMBO J., 2000, 19:6311-6316) shows a striking similarity to subunit 1 of both bacterial and bovine cytochrome c oxidase (Iwata et al., Nature, 1995, 376:660-669; Tsukihara et al., Science, 1996, 272:1136-1144), in spite of the fact that there is neither any shared functional property nor any sequence similarity between MGST1 and subunit 1 of cytochrome c oxidase. In addition, the sequence of the mPGES-1 shares more than 73% of identity with MGST1 sequence confirming thus, that the topology of the mPGES-1 is similar to MGST1 structure. Accordingly, in the present studies the structural information previously deduced for cytochrome c oxidase was used to extrapolate information required to build three-dimensional models of the mPGES-1 trimer.

As previously noted, the present studies have provided a three-dimensional model of the SBD of mPGST-1. This model was superimposed to the subunit 1 of the template (the X-ray crystal structure of cytochrome c oxidase, i.e. 1OCC.pdb). The same three-dimensional model of the SBD of mPGST-1 was also superimposed to the subunits 2 and 3 of the template. Thus, the constructed mPGES-1 trimer model has three equivalent SBDs with an approximate C3-fold symmetry. Depicted in FIG. 11 are different views of the constructed three-dimensional model #1 (FIG. 11, panel (a), panel (b) and panel (c)) of the mPGES-1 trimer complexed with GSH and PGH2.

three-dimensional model #2 (see FIG. 13) is a pure homology model modeled based on the template (the X-ray crystal structure of cytochrome c oxidase, i.e. 1OCC.pdb). The homology model of the mPGES-1 trimer was constructed using the Homology module of InsightII program, based on the individual sequence/template alignments (see FIG. 12). The alpha-helices are underlined in the sequence alignment of mPGES-1 with the cytochrome c template shown in FIG. 12. The refined final alignments based on the secondary structure of each unit were used for constructing homology models of human mPGES-1 using MODELER module of InsightII program. MODELER is a well-known comparative modeling methodology, which generates a refined three-dimensional homology model of a protein sequence automatically and rapidly, based on a given sequence alignment to a known three-dimensional protein structure.

The obtained initial three-dimensional models of the mPGES-1 trimer were refined further through carefully performing the energy-minimizations and constrained molecular dynamics (MD) simulations. FIG. 13 shows the obtained three-dimensional model #2 of the mPGES-1 trimer complexed with an inhibitor (i.e. MK-886 reported in literature) in each SBD.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

In addition, it is understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

A number of embodiments of the invention have been described. Nevertheless, it will be understood that various modifications may be made without departing from the spirit and scope of the invention. Accordingly, other embodiments are within the scope of the following claims.

What is claimed is:

1. A method of structure-based identification of candidate compounds for regulation of interactions of mPGES-1 with its cognate ligands, comprising:
   a) providing, by a processor, a three dimensional structural representation of a mPGES-1 trimer and PGH2 and/or GSH wherein PGH2 interacts with GSH through hydrogen bonding between the peroxy group of PGH2 and the —SH group of GSH and wherein:
      i) each monomer of the trimer comprises a three-dimensional structural representation of a mPGES-1 substrate binding domain (SBD) wherein:
         a) amino acid residues Q36, R110, T114, Y130, and Q134 of mPGES-1 are associated with the prostaglandin H2 (PGH2)-binding site of the SBD;
         b) amino acid residue Y130 of mPGES-1 is associated with the peroxy head of PGH2 when PGH2 occupies at least a portion of the binding site;
         c) amino acid residue Y130 of mPGES-1 is associated with the —SH group of glutathione (GSH) when GSH occupies at least a portion of the binding site;
         d) amino acid residues R110, T114, and Q36 of mPGES-1 are associated with the carboxyl tail of PGH2;
         e) the calculated binding free energy (ΔG) for an SBD-PGH2 complex is between −5.0 kcal/mol and −9.0 kcal/mol; and
         f) the calculated binding free energy (ΔG) for an SBD-GSH complex is between −4.0 kcal/mol and −8.0 kcal/mol; and;
      ii) the trimer comprises a $C_3$-fold symmetry; and
      iii) the representation of the trimer comprises a homology model based on the crystallographic structure of subunit 1 of cytochrome c oxidase; and
   b) identifying, by a processor, at least one candidate compound that interacts with the three dimensional structural representation of a) wherein said candidate has complementarity with at least one of the amino acid residues Q36, R110, T114, Y130, and Q134, and
   c) synthesizing the at least one candidate compound and determining the activity of the at least one candidate compound on m-PGES1 in vitro or in vivo.

2. A method according to claim 1, wherein the step a) comprises accessing the representation from a database or other source; importing the representation into a computer or other database; and/or displaying the representation.

3. A method according to claim 1, wherein the step b) comprises screening compounds from an available library and selecting the at least one candidate compound from the screened compounds.

4. A method according to claim 1, wherein the step b) comprises designing at least one new compound and selecting the at least one candidate compound from the at least one new compound.

5. A method according to claim 1, further comprising modifying, by a processor, the at least one candidate compound by substituting at least one atom or group of atoms to provide at least one modified compound and determining, by a processor, whether the at least one modified compound interacts with the three dimensional structural representation.

6. A method according to claim 1, wherein step b) comprises identifying at least one candidate compound that has complementarity with the amino acid residues R110, T114, and Y130.

7. A method according to claim 1, wherein step b) comprises identifying at least one candidate compound that has complementarity with the amino acid residues Q36, R110, and T114.

8. A method according to claim 1, wherein step b) comprises identifying at least one candidate compound that has complementarity with the amino acid residues Q36, R110, T114, Y130, and Q134.

9. A method according to claim 1, wherein in the three dimensional structural representation of the mPGES-1 SBD, V29, V30, I33, and V37 of mPGES-1 are associated with the carboxyl tail of PGH2 when PGH2 occupies at least a portion of the binding site.

10. A method according to claim 1, wherein in the three dimensional structural representation of the mPGES-1 SBD, K120 of mPGES-1 is associated with the peroxy head of PGH2 when PGH2 occupies at least a portion of the binding site.

11. A method according to claim 1, wherein in the three dimensional structural representation of the mPGES-1 SBD, Y80, L118, K120, L121, P124, R126, and Y130 of mPGES-1 are associated with GSH when GSH occupies at least a portion of the binding site.

12. A method according to claim 1, wherein in the three dimensional structural representation of the mPGES-1 SBD R126 of mPGES-1 is associated with the carboxy group on the Gly-end of GSH when GSH occupies at least a portion of the binding site.

13. A method according to claim 1, wherein in the three dimensional structural representation of the mPGES-1 SBD K120 and L121 of mPGES-1 are associated with the carboxyl group of the gamma-Glu-end of GSH when GSH occupies at least a portion of the binding site.

14. A method of structure-based identification of candidate compounds for regulation of interactions of mPGES-1 with its cognate ligands, comprising:
   a) providing, by a processor, a three dimensional structural representation of a mPGES-1 substrate binding domain (SBD) and PGH2 and/or GSH, wherein PGH2 interacts with GSH through hydrogen bonding between the peroxy group of PGH2 and the —SH group of GSH and, wherein:
      a) amino acid residues Q36, R110, T114, Y130, and Q134 of mPGES-1 are associated with the prostaglandin H2 (PGH2)-binding site of the SBD;
      b) amino acid residue Y130 of mPGES-1 is associated with the peroxy head of PGH2 when PGH2 occupies at least a portion of the binding site;
      c) amino acid residue Y130 of mPGES-1 is associated with the —SH group of glutathione (GSH) when GSH occupies at least a portion of the binding site;
      d) amino acid residues R110, T114, and Q36 of mPGES-1 are associated with the carboxyl tail of PGH2;
      e) the calculated binding free energy (AG) for an SBD-PGH2 complex is between −5.0 kcal/mol and −9.0 kcal/mol; and
      f) the calculated binding free energy (AG) for an SBD-GSH complex is between −4.0 kcal/mol and −8.0 kcal/mol; and
   b) identifying, by a processor, at least one candidate compound that interacts with the three dimensional structural representation of a) wherein said candidate has complementarity with at least one of the amino acid residues Q36, R110, T114, Y130, and Q134, and
   c) synthesizing the at least one candidate compound and determining the activity of the at least one candidate compound on m-PGES1 in vitro or in vivo.

15. A method according to claim 14, wherein the step a) comprises accessing the representation from a database or other source; importing the representation into a computer or other database; and/or displaying the representation.

16. A method according to claim 14, wherein the step b) comprises screening compounds from an available library and selecting the at least one candidate compound from the screened compounds.

17. A method according to claim 14, wherein the step b) comprises designing at least one new compound and selecting the at least one candidate compound from the at least one new compound.

18. A method according to claim 14, further comprising modifying, by a processor, the at least one candidate compound by substituting at least one atom or group of atoms to provide at least one modified compound and determining, by a processor, whether the at least one modified compound interacts with the three dimensional structural representation of a).

19. A method according to claim 14, wherein step b) comprises identifying at least one candidate compound that has complementarity with the amino acid residues R110, T114, and Y130.

20. A method according to claim 14, wherein step b) comprises identifying at least one candidate compound that has complementarity with the amino acid residues Q36, R110, and T114.

21. A method according to claim 14, wherein step b) comprises identifying at least one candidate compound that has complementarity with the amino acid residues Q36, R110, T114, Y130, and Q134.

22. A method according to claim 14, wherein in the three dimensional structural representation of the mPGES-1 SBD, V29, V30, I33, and V37 of mPGES-1 are associated with the carboxyl tail of PGH2 when PGH2 occupies at least a portion of the binding site.

23. A method according to claim 14, wherein in the three dimensional structural representation of the mPGES-1 SBD, K120 of mPGES-1 I is associated with the peroxy head of PGH2 when PGH2 occupies at least a portion of the binding site.

24. A method according to claim 14, wherein in the three dimensional structural representation of the mPGES-1 SBD, Y80, L118, K120, L121, P124, R126, and Y130 of mPGES-1 are associated with GSH when GSH occupies at least a portion of the binding site.

25. A method according to claim 14, wherein in the three dimensional structural representation of the mPGES-1 SBD R126 of mPGES-1 is associated with the carboxy group on the Gly-end of GSH when GSH occupies at least a portion of the binding site.

26. A method according to claim 14, wherein in the three dimensional structural representation of the mPGES-1 SBD K120 and L121 of mPGES-1 are associated with the SBD wherein K120 and L121 are associated with the carboxyl group of the gamma-Glu-end of GSH when GSH occupies at least a portion of the binding site.

* * * * *

SEQUENCE LISTING

<160> NUMBER OF SEQ ID NOS: 13

<210> SEQ ID NO 1
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 1
gtggccatca tcacgggcga agtgaggctg cggaagaag                          39

<210> SEQ ID NO 2
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 2
cttcttccgc agcctcactt cgcccgtgat gatggccac                          39

<210> SEQ ID NO 3
<211> LENGTH: 39
<212> TYPE: DNA
<213> ORGANISM: Artificial Sequence -continued

```
<220> FEATURE:
<223> OTHER INFORMATION: Oligonucleotide primer sequence

<400> SEQUENCE: 3
ctggtcttcc tcgtgggcac tgtggcacac accgtggcc                              39

<210> SEQ ID NO 4
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 4
ggccacggtg tgtgccacag tgcccacgag gaagaccag                              39

<210> SEQ ID NO 5
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 5
gtgggccgtg tggcacacgt cgtggcctac ctggggaag                              39

<210> SEQ ID NO 6
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 6
cttccccagg taggccacga cgtgtgccac acggcccac                              39

<210> SEQ ID NO 7
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 7
cccatccgct ccgtgaccat caccctggcc cagctcccc                              39

<210> SEQ ID NO 8
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 8
ggggagctgg gccagggtga tggtcacgga gcggatggg                              39

<210> SEQ ID NO 9
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 9
gtgacctaca ccctggccga gctcccctgc gcctccatg                              39
```

```
<210> SEQ ID NO 10
<211> LENGTH: 39
<212> TYPE: DNA
<213> ORGANISM: Artificial Sequence
<220> FEATURE:
<223> OTHER INFORMATION: Oligonucleotide primer sequence

<400> SEQUENCE: 10
catggaggcg cagggagct cggccagggt gtaggtcac                              39

<210> SEQ ID NO 11
<211> LENGTH: 173
<212> TYPE: PRT
<213> ORGANISM: Tarsius bancanus

<400> SEQUENCE: 11
```

Met Phe Ile Asn Arg Trp Leu Phe Ser Thr Asn His Lys Asp Ile Gly
1               5                   10                  15

Thr Leu Tyr Leu Leu Phe Gly Ala Trp Ala Gly Met Val Gly Thr Ala
            20                  25                  30

Leu Ser Leu Leu Ile Arg Ala Glu Leu Gly Gln Pro Gly Thr Leu Leu
        35                  40                  45

Gly Asp Asp Gln Ile Tyr Asn Val Val Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Phe Leu Leu Leu
            100                 105                 110

Ala Ser Ser Met Val Glu Ala Gly Ala Gly Thr Gly Trp Thr Val Tyr
        115                 120                 125

Pro Pro Leu Ala Gly Asn Leu Ala His Ala Gly Ala Ser Val Asp Leu
    130                 135                 140

Thr Ile Phe Ser Leu His Leu Ala Gly Val Ser Ser Ile Leu Gly Ala
145                 150                 155                 160

Ile Asn Phe Ile Thr Thr Ile Ile Asn Met Lys Pro Pro
                165                 170

```
<210> SEQ ID NO 12
<211> LENGTH: 152
<212> TYPE: PRT
<213> ORGANISM: Homo Sapiens

<400> SEQUENCE: 12
```

Met Pro Ala His Ser Leu Val Met Ser Ser Pro Ala Leu Pro Ala Phe
1               5                   10                  15

Leu Leu Cys Ser Thr Leu Leu Val Ile Lys Met Tyr Val Val Ala Ile
            20                  25                  30

Ile Thr Gly Gln Val Arg Leu Arg Lys Lys Ala Phe Ala Asn Pro Glu
        35                  40                  45

Asp Ala Leu Arg His Gly Gly Pro Gln Tyr Cys Arg Ser Asp Pro Asp
    50                  55                  60

Val Glu Arg Cys Leu Arg Ala His Arg Asn Asp Met Glu Thr Ile Tyr
65                  70                  75                  80

Pro Phe Leu Phe Leu Gly Phe Val Tyr Ser Phe Leu Gly Pro Asn Pro
                85                  90                  95

```
Phe Val Ala Trp Met His Phe Leu Val Phe Leu Val Gly Arg Val Ala
                100             105             110

His Thr Val Ala Tyr Leu Gly Lys Leu Arg Ala Pro Ile Arg Ser Val
        115             120             125

Thr Tyr Thr Leu Ala Gln Leu Pro Cys Ala Ser Met Ala Leu Gln Ile
    130             135             140

Leu Trp Glu Ala Ala Arg His Leu
145             150

<210> SEQ ID NO 13
<211> LENGTH: 155
<212> TYPE: PRT
<213> ORGANISM: Homo Sapiens

<400> SEQUENCE: 13

Met Val Asp Leu Thr Gln Val Met Asp Asp Glu Val Phe Met Ala Phe
1               5                   10                  15

Ala Ser Tyr Ala Thr Ile Ile Leu Ser Lys Met Met Leu Met Ser Thr
                20                  25                  30

Ala Thr Ala Phe Tyr Arg Leu Thr Arg Lys Val Phe Ala Asn Pro Glu
            35                  40                  45

Asp Cys Val Ala Phe Gly Lys Gly Glu Asn Ala Lys Lys Tyr Leu Arg
        50                  55                  60

Thr Asp Asp Arg Val Glu Arg Val Arg Lys Ala His Leu Asn Asp Leu
65                  70                  75                  80

Glu Asn Ile Ile Pro Phe Leu Gly Ile Gly Leu Leu Tyr Ser Leu Ser
                85                  90                  95

Gly Pro Asp Pro Ser Thr Ala Ile Leu His Phe Arg Leu Phe Val Gly
                100             105             110

Ala Arg Ile Tyr His Thr Ile Ala Tyr Leu Thr Pro Leu Pro Gln Pro
            115             120             125

Asn Arg Ala Leu Ser Phe Phe Val Gly Tyr Gly Val Thr Leu Ser Met
        130             135             140

Ala Tyr Arg Leu Leu Lys Ser Lys Leu Tyr Leu
145             150             155
```